(12) United States Patent
Carter et al.

(10) Patent No.: US 6,686,449 B2
(45) Date of Patent: Feb. 3, 2004

(54) MUTANT PRESENILIN 1 POLYPEPTIDES

(75) Inventors: Donald Bainbridge Carter, Kalamazoo, MI (US); Alfredo Giuseppe Tomasselli, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/896,621

(22) Filed: Jun. 29, 2001

(65) Prior Publication Data

US 2003/0065141 A1 Apr. 3, 2003

Related U.S. Application Data

(60) Provisional application No. 60/215,345, filed on Jun. 30, 2000.

(51) Int. Cl.$^7$ .......................... C07K 7/00; C07K 14/00; C07K 17/00; A61K 38/00; A61K 31/33; A01N 43/00; C12P 21/06; C12N 1/20; C12N 15/00; C12N 5/02
(52) U.S. Cl. .......................... 530/350; 530/300; 514/2; 514/12; 514/183; 424/94.1; 435/69.1; 435/252.3; 435/320.1; 435/325
(58) Field of Search .......................... 435/69.1, 320.1, 435/252.3, 325; 514/2, 12, 183; 424/94.1; 530/300, 350

(56) References Cited

U.S. PATENT DOCUMENTS

| | | | |
|---|---|---|---|
| 5,175,384 A | 12/1992 | Krimpenfort et al. | .......... 800/2 |
| 5,612,486 A | 3/1997 | McConlogue et al. | .......... 800/2 |
| 5,750,349 A | 5/1998 | Suzuki et al. | ................. 435/7.1 |
| 5,850,003 A | 12/1998 | McLonlogue et al. | .......... 800/2 |

FOREIGN PATENT DOCUMENTS

| | | | |
|---|---|---|---|
| EP | 0 367 566 | 5/1990 | ............ C12N/15/12 |
| EP | 0 811 695 | 12/1997 | ............ C12N/15/12 |
| WO | WO 91/18982 | 12/1991 | ............ C12N/15/12 |
| WO | WO 97/09433 | 3/1997 | ............ C12N/15/54 |
| WO | WO 00/17369 | 3/2000 | ............ C12N/15/57 |

OTHER PUBLICATIONS

Ngo et al. (1995) The Protein Folding Problem and Tertiary Structure Prediction. 433–506.*
Jobling et al, Mol. Microbiol., 1991, 5(7):1755–67.*
Skolnick and Fetrow (2000) From Genes to Protein Strucuture and Function: Novel Applications of Compuational Approaches in the Genomic Era. Trends in Biotech 18(1); 34–39.*
Wells, J.A. Additivity of Mutational Effects of Proteins (1990) Biochemistry 29(37): 8509–8517.*
Bork (2000) Powers and Pitfalls in Sequence Analysis: The 70% Hurdle, Genome Research 19: 398–400.*
Doerks (1998) Protein Annotation: detective work for function prediction. TIG 14(6): 248–250.*
Smith and Zhang (1997) The Challenges of genome sequence annotation of "The Devil is in the details". Nature Biotechnology 15: 1222–1223.*
Brenner (1999) Erros in genome annotation. TIG 15(4): 132–133.*
Bork and Bairoch (1996) Go Hunting in sequence databases but watch out for the traps. TIG 12(10): 425–427.*
Russo C; Schettini G; Saido TC; Hulette C; Lippa C; Lannfelt L; Ghetti B; Gambetti P; Tabaton M; Teller JK, reply: Alzheimer's disease Molecular consequences of pre-senilin–1 mutation, Nature Jun 7, 2001; 411 (6838): 655.
Ausubel, et al., ed., in Short Protocols in Molecular Biology, 2nd Edition, John Wiley & Sons, publishers, p. 16–49, 1992.
Borchelt et al., Familial Alzheimer's Disease–Linked Presenilin 1 Variants Elevate Aβ1–42/1–40 Ratio in Vitro and in Vivo *Neuron 17:* 1005–1013, 1996.
Citron, M. et al., Mutation of the beta–amyloid precursor protein in familial Alzheimer's disease increases beta–protein production. *Nature* 360, 672–674 (1992).
Citron, M.; Westaway, D.; Xia, W.; Carlson, G.; Diehl, T.; Levesque, G.; Johnson–Wood, K.; Lee, M.; Seubert, P.; Davis, A.; Kholodenko, D.; Motter, R.; Sherrington, R.; Perry, B.; Yao, H.; Strome, R.; Lieberburg, I.; Rommens, J.; Kim. S.; Schenk, D.; Fraser, P., St George Hyslop, P.; Selkoe, D.J.: Mutant presenilins of Alzheimer's disease increase production of 42–residue amyloid beta–protein in both transfected cells and transgenic mice. Nature Med. 3: 67–72, 1997.
Cosman et al., High Level Stable Expression of Human Interleukin–2 Receptors in Mouse Cells Generates Only Low Affinity Interleukin–2 Binding Sites. *Molecular Immunology.* 23:935, 1986.
Cosman et al., Cloning Sequence and Expression of Human Interleukin–2 Receptor. *Nature 312:*768, 1984.
Creighton, TE, Proteins—Structure and Molecular Properties, 2nd Ed. W. H. Freeman and Company, New York, 1993.
De Strooper B, Saftig P, Craessaerts K, Vanderstichele H, Guhde G, Annaert W, Von Figura K, Van Leuven F. Deficiency of presenilin–1 inhibits the normal cleavage of amyloid precursor protein. *Nature.* 39(6665):387–90 Jan. 22, 1998.
Gandy S; Naslund J; Nordstedt C, Alzheimer's disease Molecular consequences of presenilin–1 mutation, *Nature* 411 (6838): 654–5 Jun. 7, 2001.
Glenner GG; Wong CW, Alzheimer's disease and Down's syndrome: sharing of a unique cerebrovascular amyloid fibril protein., Biochem Biophys Res Commun Aug. 16, 1984; 122 (3): 1131–5.

(List continued on next page.)

*Primary Examiner*—Elizabeth Kemmerer
*Assistant Examiner*—Christopher James Nichols
(74) *Attorney, Agent, or Firm*—Edward F. Rehberg

(57) ABSTRACT

The present invention provides mutant presenilin 1 and presenilin 2 polpeptides and polynucleotides encoding the polypeptides and methods for their production by recombinant and PCR techniques are disclosed. Methods for utilizing the mutant polypeptides in screens for inhibitors of activity are also disclosed.

5 Claims, 10 Drawing Sheets

OTHER PUBLICATIONS

Gluzman et al., SV40–Transformed Simian Cells Support the Replication of Early SV40 Mutants. *Cell* 23:175, 1981.

Goate, A.; Chartier–Harlin, M.–C.; Mullan, M.; Brown, J.; Crawford, F.; Fidani, L.; Giuffra, L.; Haynes, A.; Irving, N.; James, L.; Mant, R.; Newton, P.; Rooke, K.; Roques, P.; Talbot, C.; Pericak–Vance, M.; Roses, A.; Williamson, R.; Rossor, M.; Owen, M.; Hardy, J.: Segregation of a missense mutation in the amyloid precursor protein gene with familial Alzheimer's disease. Nature 349: 704–706, 1991.

Hardy, John. Framing β–amyloid. *Nature Genetics.* 1:233–234, 1992.

Hogan et al., Manipulating The Mouse Embryo, Cold Spring Harbor Laboratory Press, 1986.

Kang et al. The Precursor of Alzheimer's Disease amyloid A4 Protein resembles a cell–surface receptor. *Nature* 325:733–736, 1987.

Kimberly, WT; Xia, Weiming; Rahmati, Talat; Wolfe, Michael S; Selkoe, Dennis J., The Transmembrane Aspartates in Presenilin 1 and 2 are Obligatory for γ–Secretase Activity and β–Protein Generation, vol. 275, No. 5, Feb. 4, pp. 3173–3178. Journal of Biological Chemistry (2000).

Kitaguchi et al. Novel Precursor of Alzheimer's Disease amyloid Protein shows Protease Inhibitory Activity. *Nature* 331:530–532, 1988.

Kraemer et al., Genetic Manipulation Of The Early Mammalian Embryo, Cold Spring Harbor Laboratory Press, 1985.

Jones and Bendig, Rapid PCR–Cloning of Full–Length Mouse Immunoglobulin Variable Regions. *Bio/Technology,* 9: 88, 1991.

Lehninger, *Biochemistry,* Second Edition; Worth Publishers, Inc. NY:NY pp. 71–77, 1975.

Levy–Lehad, E.; Wasco, W.; Poorkaj, P.; Romano, D. M.; Oshima, J.; Pettingell, W. H.; Yu, C.; Jondro, P. D.; Schmidt, S. D.; Wang, K.; Crowley, A. C.; Fu, Y.–H.; Guenette, S. Y.; Galas, D.; Nemens, E.; Wijsman, E. M.; Bird, T. D.; Schellenberg, G. D.; Tanzi, R.E. : Candidate gene for the chromosome 1 familial Alzheimer's disease locus. *Science* 269: 973–977, 1995.

Li YM, Xu M, Lai MT, Huang Q, Castro JL, DiMuzio–Mower J, Harrison T, Lellis C, Nadin A, Neduvelil JG, Register RB, Sardana MK, Shearman MS, Smith AL, Shi XP, Yin KC, Shafer JA, Gardell SJ. Photoactivated gamma–secretase inhibitors directed to the active site covalently label presenilin 1. *Nature.* 405(6787):689–94, Jun. 8, 2000.

Luckow, Verne A., and Max D. Summers, Trends in the Development of Baculovirus Expression Vectors *Bio/Technology* 6:47, 1988.

Marambaud P; Ancolio K; Lopez–Perez E; Checler F, Proteasome inhibitors prevent the degradation of familial Alzheimer's disease–linked presenilin 1 and potentiate A beta 42 recovery from human cells.,Molecular Medicine v.4:147–157, 1998.

Mehta ND, Refolo LM, Eckman C, Sanders S, Yager D, Perez–Tur J, Younkin S, Duff K, Hardy J, Hutton M. Increased Abeta42(43) from cell lines expressing presenilin 1 mutations. *Annals of Neurology.* 43(2):256–8, Feb. 1998.

Mullan, M., Crawford, F., Axelman, K., Houlden, H., Lilius, L., Winblad, B., Lannfelt, L. A pathogenic mutation for probable Alzheimer's disease in the APP gene at the N–terminus of beta amyloid. *Nature Genetics.* 1, 345–347 1992.

Murayama O, Tomita T, Nihonmatsu N, Murayama M, Sun S, Honda T, Iwatsubo T, Takashima A. Enhancement of amyloid 42 secretion by 28 different presenilin 1 mutations of familial Alzheimer's . *Neuroscience Letters* 265(1):61–63, Apr. 1999.

Okayama, Hiroto, and Paul Berg, A cDNA Cloning Vector That Permits Expression of cDNA Inserts in Mammalian Cells. *Molecular and Cellular Biology,* 3:280, 1983.

Ponte, P., et al., A new A4 Amyloid mRNA contains a Domain Homologous to Serine Proteinase Inhibitors. *Nature* 331:525–527, 1988.

Qian S, Jiang P, Guan XM, Singh G, Trumbauer ME, Yu H, Chen HY, Van de Ploeg LH, Zheng H. Mutant human presenilin 1 protects presenilin 1 null mouse against embryonic lethality and elevates Abeta–42/43 expression. *Neuron.* (3):611–7 Mar. 20, 1998.

Rattan et al., "Protein Synthesis: Post–translational Modifications and Aging", Ann NY Acad Sci 663:4842 1992.

Rawlings N and Barrett A, "Families of Aspartic peptidases, and those of unknown catalytic mechanism," Methods in Enzymology, vol. 248, 1995; pp. 105–120.

Rishton GM, Retz DM, Tempest PA, Novotny J, Kahn S, Treanor JJ, Lile JD, Citron M. Fenchylamine sulfonamide inhibitors of amyloid beta peptide production by the gamma–secretase proteolytic pathway: potential small–molecule therapeutic agents for the treatment of Alzheimer's disease. *J Med Chem.* 43(12):2297–9, Jun. 15, 2000.

Rogaev, E. I.; Sherrington, R.; Rogaeva, E. A.; Levesque, G.; Ikeda, M.; Liang, Y.; Chi, H.; Lin, C.; Holman, K.; Tsuda, T.; Mar, L.; Sorbi, S.; Nacmias, B.; Placentini, S.; Amaducci, L.; Chumakov, I.; Cohen, D.; Lannfelt, L.; Fraser, P. E.; Rommens, J. M.; St George–Hyslop, P. H.: Familial Alzheimer's disease in kindreds with missense mutations in a gene on chromosome 1 related to the Alzheimer's disease type 3 gene. *Nature* 376: 775–778, 1995.

Russo, C; Schettini G; Saido TC; Hulette C; Lippa C; Lannfelt L; Ghetti B; Gambetti P; Tabaton M; Teller JK, Presenilin–1 mutations in Alzheimer's disease., *Nature* 405 (6786): 531–2, Jun. 1, 2000.

Gandy, S., Nastond, J., and Nordstedt, C. "Alzheimer's disease: Molecular consequences of presenilin–1 mutation," *Nature* 411, pp. 654–655 (2001).

Seifter et al., Analysis for protein modifications and non-protein cofactors, *Methods in Enzymology* 182:626–646, 1990.

Sherrington, R.; Rogaev, E. I.; Liang, Y.; Rogaeva, E. A.; Levesque, G.; Ikeda, M.; Chi, H.; Lin, C.; Li, G.; Holman, K.; Tsuda, T.; Mar. L.; Foncin, J.–F.; Bruni, A. C.; Montesi, M. P.; Sorbi, S.; Rainero, I.; Pinessi, L.; Nee, L.; Chumakov, I.; Pollen, D.; Brookes, A.; Sanseau, P.; Polinsky, R. J.; Wasco, W.; Da Silva, H. A. R.; Haines, J. L.; Pericak–Vance, M. A.; Tanzi, R. E.; Roses, A. D.; Fraser, P. E.; Rommens, J. M.; St. George–Hyslop, P. H.: Cloning of a gene bearing mis–sense mutations in early–onset familial Alzheimer's disease. *Nature* 375: 754–760, 1995.

Suzuki, N., et al. An increased precentage of long amyloid beta protein secreted by amilial amyloid beta protein precursor (beta APP717) mutants. *Science* 264, 1336–1340, 1994.

Tajima K, Babich S, Yoshida Y, Dantes A, Strauss JF 3rd, Amsterdam A. The proteasome inhibitor MG132 promotes accumulation of the steroidogenic acute regulatory protein (StAR) and steroidogenesis. *Federation of European Biochemical Societies Letter.* 490(1–2):59–64, Feb. 9, 2001.

Tanzi, Rudolph E., Protease Inhibitor Domain Encoded by an Amyloid Protein Precursor mRNA Associated with Alzheimer's Disease. *Nature,* 331:528–530, 1988.

Wold, F., "Post–translational Protein Modifications: Perspectives and Prospects", pp. 1–12 in Postranslational Covalent Modification of Proteins, B. C. Johnson, Ed., Academic Press, New York, 1983.

Xia W, Zhang J, Kholodenko D, Citron M, Podlisny MB, Teplow DB, Haass D, Seubert P, Koo EH, Selkoe DJ. Enhanced Production and Oligomerization of the 42–residue Amyloid–Protein by Chinese Hamster Ovary Cells Stably Expressing Mutant Presenilins J. Biol. Chem. 272:7977–7982, 1997.

Yamatsuji, Tomoki, et al., G Protein–Mediated Neuronal DNA Fragmentation Induced by Familial Alzheimer's Disease–Associated Mutants of APP. *Science* 272:1349–1352, 1996.

Zigmond, Bloom, Landis, Roberts, Squire, eds. "Fundamental Neuroscience," Academic Press (1999), pp. 1333–1335.

* cited by examiner

Figure 1

```
  1 MTELPAPLSYFQNAQMSEDNHLSNTVRSQNDNRERQEHNDRRSLGHPEPL  50
  1 MTELPAPLSYFQNAQMSEDNHLSNTVRSQNDNRERQEHNDRRSLGHPEPL  50

51 SNGRPQGNSRQVVEQDEEEDEELTLKYGAKHVIMLFVPVTLCMVVVVATI 100
 51 SNGRPQGNSRQVVEQDEEEDEELTLKYGAKHVIMLFVPVTLCMVVVVATI 100

101 KSVSFYTRKDGQLIYTPFTEDTETVGQRALHSILNAAIMISVIVVMTILL 150
101 KSVSFYTRKDGQLIYTPFTEDTETVGQRALHSILNAAIMISVIVVMTILL 150

151 VVLYKYRCYKVIHAWLIISSLLLLFFFSFIYLGEVFKTYNVAVDYITVAL 200
151 VVLYKYRCYKVIHAWLIISSLLLLFFFSFIYLGEVFKTYNVAVDYITVAL 200

201 LIWNFGVVGMISIHWKGPLRLQQAYLIMISALMALVFIKYLPEWTAWLIL 250
201 LIWNFGVVGMISIHWKGPLRLQQAYLIMISALMALVFIKYLPEWTAWLIL 250

251 AVISVYDLVAVLCPKGPLRMLVETAQERNETLFPALIYSSTMVWLVNMAE 300
251 AVISVYDXXAVLCPKGPLRMLVETAQERNETLFPALIYSSTMVWLVNMAE 300

301 GDPEAQRRVSKNSKYNAESTERESQDTVAENDDGGFSEEWEAQRDSHLGP 350
301 GDPEAQRRVSKNSKYNAESTERESQDTVAENDDGGFSEEWEAQRDSHLGP 350

351 HRSTPESRAAVQELSSSILAGEDPEERGVKLGLGDFIFYSVLVGKASATA 400
351 HRSTPESRAAVQELSSSILAGEDPEERGVKLGLGDXXFYSVLVGKASATA 400

401 SGDWNTTIACFVAILIGLCLTLLLLAIFKKALPALPISITFGLVFYFATD 450
401 SGDWNTTIACFVAILIGLCLTLLLLAIFKKALPALPISITFGLVFYFATD 450

451 YLVQPFMDQLAFHQFYI 467
451 YLVQPFMDQLAFHQFYI 467
```

Figure 2

```
  1 MLTFMASDSEEEVCDERTSLMSAESPTPRSCQEGRQGPEDGENTAQWRSQ  50
    ||||||||||||||||||||||||||||||||||||||||||||||||||
  1 MLTFMASDSEEEVCDERTSLMSAESPTPRSCQEGRQGPEDGENTAQWRSQ  50

51 ENEEDGEEDPDRYVCSGVPGRPPGLEEELTLKYGAKHVIMLFVPVTLCMI 100
    ||||||||||||||||||||||||||||||||||||||||||||||||||
 51 ENEEDGEEDPDRYVCSGVPGRPPGLEEELTLKYGAKHVIMLFVPVTLCMI 100

101 VVVATIKSVRFYTEKNGQLIYTTFTEDTPSVGQRLLNSVLNTLIMISVIV 150
    ||||||||||||||||||||||||||||||||||||||||||||||||||
101 VVVATIKSVRFYTEKNGQLIYTTFTEDTPSVGQRLLNSVLNTLIMISVIV 150

151 VMTIFLVVLYKYRCYKFIHGWLIMSSLMLLFLFTYIYLGEVLKTYNVAMD 200
    ||||||||||||||||||||||||||||||||||||||||||||||||||
151 VMTIFLVVLYKYRCYKFIHGWLIMSSLMLLFLFTYIYLGEVLKTYNVAMD 200

151 VMTIFLVVLYKYRCYKFIHGWLIMSSLMLLFLFTYIYLGEVLKTYNVAMD 200
    ||||||||||||||||||||||||||||||||||||||||||||||||||
151 VMTIFLVVLYKYRCYKFIHGWLIMSSLMLLFLFTYIYLGEVLKTYNVAMD 200

201 YPTLLLTVWNFGAVGMVCIHWKGPLVLQQAYLIMISALMALVFIKYLPEW 250
    ||||||||||||||||||||||||||||||||||||||||||||||||||
201 YPTLLLTVWNFGAVGMVCIHWKGPLVLQQAYLIMISALMALVFIKYLPEW 250

251 SAWVILGAISVYDLVAVLCPKGPLRMLVETAQERNEPIFPALIYSSAMVW 300
    |||||||||||||  |||||||||||||||||||||||||||||||||||
251 SAWVILGAISVYDXXAVLCPKGPLRMLVETAQERNEPIFPALIYSSAMVW 300

301 TVGMAKLDPSSQGALQLPYDPEMEEDSYDSFGEPSYPEVFEPPLTGYPGE 350
    ||||||||||||||||||||||||||||||||||||||||||||||||||
301 TVGMAKLDPSSQGALQLPYDPEMEEDSYDSFGEPSYPEVFEPPLTGYPGE 350

351 ELEEEEERGVKLGLGDFIFYSVLVGKAAATGSGDWNTTLACFVAILIGLC 400
    ||||||||||||||||  ||||||||||||||||||||||||||||||||
351 ELEEEEERGVKLGLGDXXFYSVLVGKAAATGSGDWNTTLACFVAILIGLC 400

401 LTLLLLAVFKKALPALPISITFGLIFYFSTDNLVRPFMDTLASHQLYI   448
    ||||||||||||||||||||||||||||||||||||||||||||||||
401 LTLLLLAVFKKALPALPISITFGLIFYFSTDNLVRPFMDTLASHQLYI   448
```

MUTANT PRESENILIN 1 POLYPEPTIDES

CROSS REFERENCE TO RELATED APPLICATIONS

This application claims the benefit of the following provisional application: Application Ser. No. 60/215345 filed Jun. 30, 2000 under 35 U.S.C 119(e)(1).

FIELD OF THE INVENTION

The present invention provides mutant presenilin 1 and presenilin 2 polypeptides and polynucleotides encoding the polypeptides and methods for their production by recombinant and PCR techniques are disclosed. Methods for utilizing the mutant polypeptides in cell based and in-vitro assays for inhibitors of activity are also disclosed.

BACKGROUND OF THE INVENTION

Alzheimer's disease was originally thought to be a rare disorder primarily affecting only people under the age of 65. It is now recognized as the most common form of dementia, and alone is responsible for about 50% of all dementias; an additional 15–20% of dementias have combined Alzheimer's and vascular pathology.

The prevalence of the Alzheimer's is directly related to age. It can occur in the fourth decade of life but is extraordinarily rare at this age. The prevalence then increases logarithmically with each succeeding decade. Over the age of 85 at least one person in four is afflicted. Because persons over the 85 form the rapidly growing portion of the population Alzheimer's disease represents a major health problem. Zigmond, et.: Fundamental Neuroscience, Academic Press, 1999.

Alzheimer's disease is thought to be initiated by the deposition of amyloid plaque in cortex and hippocampus. The material deposited in plaque is proteinaceous. It consists primarily of the amyloid β-peptide (Aβ), a peptide of 39–43 amino acids which is derived from a larger precursor, the amyloid peptide precursor (APP), through the action of specific proteases. APP is a large, type-I transmembrane protein of 695–770 amino acids that is expressed by a variety of cell types including neurons, glia and somatic cells. The cleavage of Aβ from APP is accomplished by the action of two proteolytic activities commonly denoted as beta-secretase (Asp2) and gamma-secretase. Processing at the γ-secretase site is somehow dependent on presenilin-1 (as it does not occur in PS1 null embryonic neurons grown in culture, DeStrooper et al., 1997), but the protease responsible has not been identified. Deletion of the PS1 gene in mice greatly reduces gamma secretase activity. With less than 5% of the APP made by the cell processed through the amyloidogenic pathway to Aβ. DeStrooper (1998); Qian (1998).

A causative role for Aβ peptide in Alzheimer's disease is supported by genetic studies of familial, early-onset Alzheimer's disease in which inheritance follows an autosomal dominant mode of transmission. In such patients, genetic forms of Alzheimer's disease have been associated with mutations in the APP gene (Groate et al., 1991; Mullan et al. 1992), and two related genes, presenilin-1 (PS-1; Sherrington et al., 1995) and presenilin-2 (PS-2; Levy-Lahad et al., 1995; Rogaev et al., 1995). Mutations in all three genes alter production of the Aβ peptide in specific ways.

PS1 and PS2 mutations subtly increase the production of $A\beta_{1-42}$ peptide as compared to the $A\beta_{1-40}$ peptide (e.g., Citron et al., 1997), Mehta et al. (1998), Murayama et al. (1999), Xia et al. (1997). $A\beta_{1-42}$ is generally recognized as being more toxic to cells than $A\beta_{1-40}$.

Because PS1 and PS2 are intimately involved with the processing of APP both genes are attractive targets for drug screening in which aberrant APP processing is a causative or exacerbating factor. It has been postulated that both presenilin 1 and presenilin 2 have some intrinsic protease activity but this activity is so weak that designing a method of screening test agents which inhibit the intrinsic activity is problematic. The invention provides mutant presenilin 1 and presenilin 2 with enhanced proteolytic activities suitable for high throughput screening.

Literature Cited

1. Citron, M. et al. Mutation of the beta-amyloid precursor protein in familial Alzheimer's disease increases beta-protein production. Nature 360, 372–374 (1992).
2. Citron, M.; Westaway, D.; Xia, W.; Carlson, G.; Diehl, T.; Levesque, G.; Johnson-Wood, K.; Lee, M.; Seubert, P.; Davis, A.; Kholodenko, D.; Motter, R.; Sherrington, R.; Perry, B.; Yao, H.; Strome, R.; Lieberburg, I.; Rommens, J.; Kim. S.; Schenk, D.; Fraser, P.; St George Hyslop, P.; Selkoe, D. J. : Mutant presenilins of Alzheimer's disease increase production of 42-residue amyloid beta-protein in both transfected cells and transgenic mice. Nature Med. 3: 67–72, 1997.
3. De Strooper B, Saftig P, Craessaerts K, Vanderstichele H, Guhde G, Annaert W, Von Figura K, Van Leuven F. Deficiency of presenilin-1 inhibits the normal cleavage of amyloid precursor protein. Nature. Jan. 22, 1998 ;391 (6665):387–90
4. Goate, A.; Chartier-Harlin, M.-C.; Mullan, M.; Brown, J.; Crawford, F.; Fidani, L.; Giuffra, L.; Haynes, A.; Irving, N.; James, L.; Mant, R.; Newton, P.; Rooke, K.; Roques, P.; Talbot, C.; Pericak-Vance, M.; Roses, A.; Williamson, R.; Rossor, M.; Owen, M.; Hardy, J. : Segregation of a missense mutation in the amyloid precursor protein gene with familial Alzheimer's disease. Nature 349: 704-706, 1991
5. Levy-Lahad, E.; Wasco, W.; Poorkaj, P.; Romano, D. M.; Oshima, J.; Pettingell, W. H.; Yu, C.; Jondro, P. D.; Schmidt, S. D.; Wang, K.; Crowley, A. C.; Fu, Y.-H.; Guenette, S. Y.; Galas, D.; Nemens, E.; Wijsman, E. M.; Bird, T. D.; Schellenberg, G. D.; Tanzi, R. E. : Candidate gene for the chromosome 1 familial Alzheimer's disease locus. Science 269: 973-977, 1995.
6. Mehta N D, Refolo L M, Eckman C, Sanders S, Yager D, Perez-Tur J, Younkin S, Duff K, Hardy J, Hutton M. Increased Abeta42(43) from cell lines expressing presenilin 1 mutations. Ann.Neurol. 1998 Feb; 43(2):256–8.
7. Murayama O, Tomita T, Nihonmatsu N, Murayama M, Sun S, Honda T, Iwatsubo T, Takashima A. Enhancement of amyloid 42 secretion by 28 different presenilin 1 mutations of familial Alzheimer's. Neuroscience Letters 1999 April; 265 (1):61–63.
8. Mullan, M., Crawford, F., Axelman, K., Houlden, H., Lilius, L., Winblad, B., Lannfelt, L. A pathogenic mutation for probable Alzheimer's disease in the APP gene at the N-terminus of beta amyloid. Nat Genet. 1, 345–347 (1992).
9. Rogaev, E. I.; Sherrington, R.; Rogaeva, E. A.; Levesque, G.; Ikeda, M.; Liang, Y.; Chi, H.; Lin, C.; Holman, K.; Tsuda, T.; Mar, L.; Sorbi, S.; Nacmias, B.; Placentini, S.; Amaducci, L.; Chumakov, I.; Cohen, D.; Lannfelt, L.; Fraser, P. E.; Rommens, J. M.; St George-Hyslop, P. H. : Familial Alzheimer's disease in kindreds with missense mutations in a gene on chromosome 1 related to the Alzheimer's disease type 3 gene. Nature 376: 775–778, 1995.

10. Sherrington, R.; Rogaev, E. I.; Liang, Y.; Rogaeva, E. A.; Levesque, G.; Ikeda, M.; Chi, H.; Lin, C.; Li, G.; Holman, K.; Tsuda, T.; Mar, L.; Foncin, J.-F.; Bruni, A. C.; Montesi, M. P.; Sorbi, S.; Rainero, I.; Pinessi, L.; Nee, L.; Chumakov, I.; Pollen, D.; Brookes, A.; Sanseau, P.; Polinsky, R. J.; Wasco, W.; Da Silva, H. A. R.; Haines, J. L.; Pericak-Vance, M. A.; Tanzi, R. E.; Roses, A. D.; Fraser, P. E.; Rommens, J. M.; St George-Hyslop, P. H. : Cloning of a gene bearing mis-sense mutations in early-onset familial Alzheimer's disease. Nature 375: 754–760, 1995.

11. Suzuki, N., et al. An increased percentage of long amyloid beta protein secreted by amilial amyloid beta protein precursor (beta APP717) mutants. *Science* 264, 1336–1340 (1994).

12. Qian S, Jiang P, Guan X M, Singh G, Trumbauer M E, Yu H, Chen H Y, Van de Ploeg L H, Zheng H. Mutant human presenilin 1 protects presenilin 1 null mouse against embryonic lethality and elevates Abeta 1-42/43 expression. Neuron. 1998 Mar; 20(3):611–7.

13. Xia W, Zhang J, Kholodenko D, Citron M, Podlisny M B, Teplow D B, Haass D, Seubert P, Koo E H, Selkoe D J. Enhanced Production and Oligomerization of the 42-residue Amyloid-Protein by Chinese Hamster Ovary Cells Stably Expressing Mutant Presenilins J. Biol. Chem. 1997;272:7977–7982.

14. Zigmond, M. J, Bloom, F. E., Landis, S. C., Roberts, J. L., Squire, L. R.:
Fundamental Neuroscience, Academic Press, 1999.

15. Li Y M, Xu M, Lai M T, Huang Q, Castro J L, DiMuzio-Mower J, Harrison T, Lellis C, Nadin A, Neduvelil J G, Register R B, Sardana M K, Shearman M S, Smith A L, Shi X P, Yin K C, Shafer J A, Gardell S J. Photoactivated gamma-secretase inhibitors directed to the active site covalently label presenilin 1. Nature. Jun. 8, 2000; 405(6787):689–94.

16. Rishton G M, Retz D M, Tempest P A, Novotny J, Kahn S, Treanor J J, Lile J D, Citron M. Fenchylamine sulfonamide inhibitors of amyloid beta peptide production by the gamma-secretase proteolytic pathway: potential small-molecule therapeutic agents for the treatment of Alzheimer's disease. J Med Chem. Jun. 15, 2000; 43(12):2297–9.

17. Tajima K, Babich S, Yoshida Y, Dantes A, Strauss J F 3rd, Amsterdam A. The proteasome inhibitor MG132 promotes accumulation of the steroidogenic acute regulatory protein (StAR) and steroidogenesis. FEBS Lett. Feb. 9, 2001; 490(1–2):59–64.

18. Marambaud P; Ancolio K; Lopez-Perez E; Checler F, Proteasome inhibitors prevent the degradation of familial Alzheimer's disease-linked presenilin 1 and potentiate A beta 42 recovery from human cells., Molecular Medicine 1998, v.4:147–157.

19. Gandy S; Naslund J; Nordstedt C, Alzheimer's disease Molecular consequences of presenilin-1 mutation, Nature Jun. 7, 2001; 411 (6838): 654–5.

20. Russo C; Schettini G; Saido T C; Hulette C; Lippa C; Lannfelt L; Ghetti B; Gambetti P; Tabaton M; Teller J K, reply: Alzheimer's disease Molecular consequences of presenilin-1 mutation, Nature Jun. 7, 2001; 411 (6838): 655

21. Russo C; Schettini G; Saido T C; Hulette C; Lippa C; Lannfelt L; Ghetti B; Gambetti P; Tabaton M; Teller J K, Presenilin-1 mutations in Alzheimer's disease., Nature Jun. 1, 2000; 405 (6786): 531–2

22. Glenner G G; Wong C W, Alzheimer's disease and Down's syndrome: sharing of a unique cerebrovascular amyloid fibril protein., Biochem Biophys Res Commun Aug. 16, 1984; 122 (3): 1131–5.

BRIEF DESCRIPTION OF THE SEQUENCE LISTINGS

SEQ ID NO:1 cDNA encoding mutant presenilin-1 (nucleotides 772–777 site directed mutagenesis sites directed by "n's)

SEQ ID NO:2 cDNA encoding mutant presenilin-1 (nucleotides 1156–1161 site directed mutagenesis sites directed by "n's)

SEQ ID NO:3 cDNA encoding mutant presenilin-1 (nucleotides 772–777 and 1156–1161 site directed mutagenesis sites directed by "n's)

SEQ ID NO:4 mutant presenilin-1 (amino acids 258–259 variable amino acids denoted by "x"'s )

SEQ ID NO:5 mutant presenilin-1 (amino acids 386–387 variable amino acids denoted by "x"'s)

SEQ ID NO:6 mutant presenilin-1 (amino acids 258–259 and 386–387 variable amino acids denoted by "x"'s)

SEQ ID NO:7 cDNA encoding mutant presenilin-2 (nucleotides 790–795 site directed mutagenesis sites directed by "n's)

SEQ ID NO:8 cDNA encoding mutant presenilin-2 (nucleotides 1099–1104 site directed mutagenesis sites directed by "n's)

SEQ ID NO:9 cDNA encoding mutant presenilin-2 (nucleotides 790–795 and 1099–1104 site directed mutagenesis sites directed by "n's)

SEQ ID NO:10 mutant presenilin-2 (amino acids 264–265 variable amino acids denoted by "x"'s)

SEQ ID NO:11 mutant presenilin-2 (amino acids 367–368 variable amino acids denoted by "x"'s)

SEQ ID NO:12 mutant presenilin-2 (amino acids 264-265 and 367–368 variable amino acids denoted by "x"'s)

SEQ ID NOS: 13–20 Mutagenesis oligonucleotides

BRIEF DESCRIPTION OF THE DRAWINGS

FIG. 1 Alignment of wild type and mutant presenilin-1 showing positions of site directed mutagenesis sites in bold type FIG. 2 Alignment of wild type and mutant presenilin-2 showing positions of site directed mutagenesis sites in bold type FIG. 3 512088 Drug Treatment and its Effect on $A\beta_{1-40}$ levels in cell lines expressing $APP_{SW}KK$ alone, $APP_{SW}KK$ and Wild-Type PS1 and $APP_{SW}KK$ and PS1 wt/DTG FIG. 4 512088 Drug Treatment and its Effect on $A\beta_{1-42}$ levels in cell lines expressing $APP_{SW}KK$ alone, $APP_{SW}KK$ and Wild-Type PS1 and $APP_{SW}KK$ and PS 1 wt/DTG FIG. 5 L685,458 Drug Treatment and its Effect on $A\beta_{1-40}$ levels in cell lines expressing $APP_{SW}KK$ alone, $APP_{SW}KK$ and Wild-Type PS1 and $APP_{SW}KK$ and PS1 wt/DTG FIG. 6 L685,458 Drug Treatment and its Effect on $A\beta_{1-42}$ levels in cell lines expressing $APP_{SW}KK$ alone, $APP_{SW}KK$ and Wild-Type PS1 and $APP_{SW}KK$ and PS1 wt/DTG FIG. 7 MG132 Drug Treatment and its Effect on $A\beta_{1-40}$ levels in cell lines expressing $APP_{SW}KK$ alone, $APP_{SW}KK$ and Wild-Type PS1 and $APP_{SW}KK$ and PS1 wt/DTG FIG. 8 MG132 Drug Treatment and its Effect on $A\beta_{1-42}$ levels in cell lines expressing $APP_{SW}KK$ alone, $APP_{SW}KK$ and Wild-Type PS1 and $APP_{SW}KK$ and PS1 wt/DTG FIG. 9 Vehicle (DMSO) Treatment and its Effect on $A\beta_{1-40}$ levels in cell lines expressing $APP_{SW}KK$ alone, $APP_{SW}KK$ and Wild-Type PS1 and APPSWKK and PS1 wt/DTG FIG. 10 Vehicle (DMSO) Treatment and its Effect on Aβ$_{1-42}$ levels in cell lines expressing APP$_{SW}$KK alone, APP$_{SW}$KK and Wild-Type PS1 and APP$_{SW}$KK and PS1 wt/DTG

SUMMARY OF THE INVENTION

Figure 3:
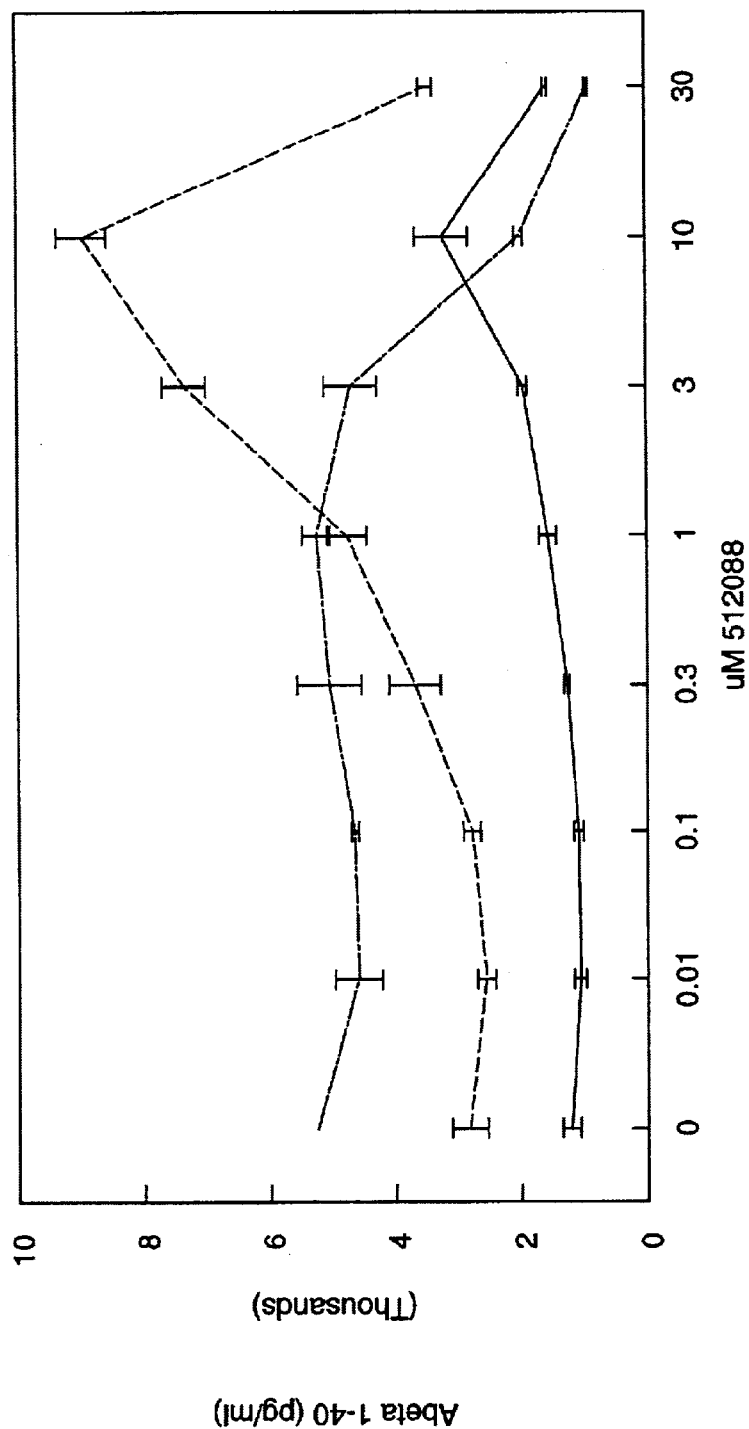

The present invention addresses the need identified above in that it provides heretofore unknown isolated mutant presenilin 1 and presenilin 2 (or herinafter "mutant PS1 and PS2) polypeptides and the isolated polynucleotide molecules that encode them, as well as vectors and host cells comprising such polynucleotide molecules.

The invention provides an isolated polypeptide comprising at least 130 contiguous amino acids of SEQ ID NO:6 including amino acid residues 258 through 387 of SEQ ID NO:6 wherein residue 258 is selected from the group consisting of leucine, threonine or conservative substitutions of threonine, and/or wherein residue 259 is selected from the group consisting of valine, glycine or conservative substitutions of, and/or wherein residue 386 is selected from the group consisting of phenylalanine, threonine or conservative substitutions of threonine and/or wherein residue 387 is selected from the group consisting of isoleucine, glycine or conservative substitutions of glycine, with the proviso that a polypeptide where amino acid residue 258 is a leucine, amino acid residue 259 is a valine, amino acid residue 386 is a phenylalanine and amino residue 387 is a isoleucine is excluded The invention is intended to encompass each and every polypeptide represented by the above description. A preferred embodiment of the invention is a polypeptide which is at least 140, at least 150, at least 160, at least 170, at least 180, at least 190, at least 200, at least 210, at least 220, at least 230, at least 240, at least 250, at least 260, at least 270, at least 280, at least 300, at least 310, at least 320, at least 330, at least 340, at least 350, at least 360, at least 370, at least 380, at least 390, at least 400, at least 410, at least 420, at least 430, at least 440, at least 450, at least 460, at least 467 amino acids in length. A particularly preferred embodiment of the polypeptide of the invention comprises a polypeptide of 467 amino acids in length.

The invention further provides, An isolated polypeptide comprising at least 110 contiguous amino acids of SEQ ID NO:12 including amino acid residues 264 through 368 of SEQ ID NO:6 wherein residue 264 is selected from the group consisting of leucine, threonine or conservative substitutions of threonine, and/or wherein residue 265 is selected from the group consisting of valine, glycine or conservative substitutions of glycine., and/or wherein residue 367 is selected from the group consisting of phenylalanine, threonine or conservative substitutions of threonine and/or wherein residue 368 is selected from the group consisting of isoleucine, glycine or conservative substitutions of glycine, with the proviso that a polypeptide where amino acid residue 258 is a leucine, amino acid residue 259 is a valine, amino acid residue 386 is a phenylalanine and amino residue 387 is a isoleucine is excluded The invention is intended to encompass each and every polypeptide represented by the above description. A preferred embodiment of the invention is a polypeptide which is at least 120, at least 130, at least 140, at least 150, at least 160, at least 170, at least 180, at least 190, at least 200, at least 210, at least 220, at least 230, at least 240, at least 250, at least 260, at least 270, at least 280, at least 300, at least 310, at least 320, at least 330, at least 340, at least 350, at least 360, at least 370, at least 380, at least 390, at least 400, at least 410, at least 420, at least 430, at least 440, at least 448 amino acids in length. A particularly preferred embodiment of the polypeptide above comprises a polypeptide of 448 amino acids in length.

The invention further provides polynucleotides encoding the polypeptides of the invention. Each and every polynucleotide encoding the polypeptides of the invention are intended to be encompassed by the invention.

In a related embodiment, the invention provides vectors comprising a polynucleotides of the invention. Such vectors are useful, e.g., for amplifying the polynucleotides in host cells to create useful quantities thereof. In other embodiments, the vector is an expression vector wherein the polynucleotide of the invention is operatively linked to a polynucleotide comprising an expression control sequence. Such vectors are useful for recombinant production of polypeptides of the invention.

In another related embodiment, the invention provides host cells that are transformed or transfected (stably or transiently) with polynucleotides of the invention or vectors of the invention. As stated above, such host cells are useful for amplifying the polynucleotides and also for expressing the mutant PS1 and PS2 polypeptides or fragments thereof encoded by the polynucleotide.

In still another related embodiment, the invention provides a method for producing a mutant PS1 or PS2 polypeptide (or fragment thereof) comprising the steps of growing a host cell of the invention in a nutrient medium and isolating the polypeptide from the cell or the medium. In still another related embodiment methods of identifying agents which modulate Aβ derived peptide production. Such methods comprise contacting amyloid precursor protein (APP) and a mutant PS1 or PS2 polypeptide in the presence and absence of a test agent; determining the amount of at least one Aβ derived peptide produced in the presence and absence of the test agent; and comparing the amount of at least one Aβ derived peptide in the presence of the test agent to the amount of at least one Aβ derived peptide in the absence of the test agent to identify an agent that modulates Aβ derived peptide production wherein differing levels of said Aβ derived peptide produced in the presence of a test agent identifies an agent that modulates Aβ production In still another related embodiment, the invention provides a method for the identification of an agent capable of altering the ratio of Aβ$_{1-40}$/(Aβ$_{1-40}$+Aβ$_{1-42}$)produced in any of the cell lines expressing mutant PS1 and PS2 polypeptides comprising the steps of: obtaining a test culture and a control culture of said cell line, contacting said test culture with a test agent, measuring the levels of Aβ$_{1-40}$ and Aβ1-42 produced by said test culture and said control culture, calculating the ratio of Aβ$_{1-40}$/(Aβ$_{1-40}$+Aβ$_{1-42}$) for said test culture and said control culture from the levels of Aβ$_{1-40}$ and Aβ$_{1-42}$ measured, and comparing the ratio of Aβ$_{1-40}$/(Aβ$_{1-40}$+Aβ$_{1-42}$) measured for said test culture and said control culture. A determination that the ratio of Aβ$_{1-40}$/(Aβ$_{1-40}$+Aβ$_{42}$) for said test culture is higher or lower than ratio of Aβ$_{1-40}$/(Aβ$_{1-40}$+Aβ$_{1-42}$) for said control culture indicates that said test agent has altered the ratio of Aβ$_{1-40}$/(Aβ$_{1-40}$+Aβ$_{1-42}$).

The invention further provides a transgenic non-human animal containing in germ or somatic cells, any of the nucleic acids described above.

The encoded polypeptides can be used as a target for the screening of drugs useful in the treatment of useful in treating pathologies associated with aberrant APP processing including Alzheimer's disease. High-throughput assays for identifying inhibitors of presenilin activity are provided. High throughput assays are provided, as are related assay compositions, integrated systems for assay screening and other features that will be evident upon review.

DETAILED DESCRIPTION OF THE INVENTION

Definitions

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

"Allelic variants" are modified forms of a wild type gene sequence, the modification resulting from recombination during chromosomal segregation or exposure to conditions which give rise to genetic mutation. Allelic variants, like wild type genes, are naturally occurring sequences (as opposed to non-naturally occurring variants which arise from in vitro manipulation).

"Isolated" as used herein and as understood in the art, whether referring to "isolated" polynucleotides or polypeptides, is taken to mean that it is uniquely created by the inventors, separated from the original cellular or genetic environment in which the polypeptide or nucleic acid is normally found. As used herein therefore, by way of example only, a transgenic animal or a recombinant cell line constructed with a polynucleotide of the invention, incorporates the "isolated" nucleic acid.

As used hereinafter "polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

As used hereinafter "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation prenylation, racemization, selenoylation, sulfation, transfer-RNA mediated addition of amino acids to proteins such as arginylation, and ubiquitination (see, for instance, Proteins-Structure and Molecular Properties, 2nd Ed., T. E. Creighton, W. H. Freeman and Company, New York, 1993; Wold, F., Post-translational Protein Modifications: Perspectives and Prospects, pgs. 1–12 in Postranslational Covalent Modification of Proteins, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann NY Acad Sci (1992) 663:4842).

As used herein, the term "test agent" means any identifiable chemical or molecule, including, but not limited to a small molecule, peptide, protein, sugar, nucleotide, or nucleic acid. Such a test agent can be natural or synthetic.

As used herein, the term "contacting" means bringing together, either directly or indirectly, a compound into physical proximity to a polypeptide or polynucleotide of the invention. The polypeptide or polynucleotide can be present in any number of buffers, salts, solutions, etc. Contacting includes, for example, placing the compound into a beaker, microtiter plate, cell culture flask, or a microarray, such as a gene chip, or the like, which contains either the ion channel polypeptide or fragment thereof, or nucleic acid molecule encoding an ion channel or fragment thereof.

The term "Aβ" (or β-amyloid peptide) refers to a 38–43 amino acid peptide having a molecular weight of about 4.2 kD, which peptide is substantially homologous to the form of the protein described by Glenner et al., Biochem. Biophys. Res. Commun. 120, 885–890, (1984) including mutations and post translational modifications of the normal β-amyloid peptide. In whatever form, the β-amyloid peptide is an approximate 38–43 amino acid fragment of a large membrane-spanning glycoprotein, referred to as the β-amyloid precursor protein (APP). β amyloid peptide also includes sequences 1–6, SEQ ID NOs. 1–6 of U.S. Pat. No. 5,750,349, issued May 12, 1998 (incorporated into this document by reference). β amyloid peptide is derived from a region of APP adjacent to and containing a portion of the transmembrane domain. Normally, processing of APP at the α-secretase site cleaves the midregion of the Aβ sequence adjacent to the membrane and releases the soluble, extracellular domain of APP from the cell surface. This α-secretase APP processing creates "soluble APPα"-, which is normal and not thought to contribute to AD. Pathological processing of APP at the β- and γ-secretase sites, which are located N-terminal and C-terminal to the α-secretase site, respectively, produces a very different result than processing at the α site. Sequential processing at the β- and γ-secretase sites releases the β amyloid peptide" (β) described above.

The term "N terminally truncated Aβ" as used herein is defined as Aβ in which N terminal amino acid residues are missing. "N terminal truncated Aβ" encompasses $A\beta_{x-38}$, $A\beta_{x-39}$, $A\beta_{1-40}$, $A\beta_{x-41}$, $A\beta_{x-42}$, and $A\beta_{x-43}$ wherein "x" is an integer greater than 1 and less than or equal to 22. Russo et al. *Nature* 405, 531–532 (2000); Russo et al. *Nature* 411, 655 (2001); Gandy et al. 411, 654–655 (2001). have characterized N terminal truncated Aβ in the brains of patients suffering from sporadic or familial Alzheimer's disease due to mutations in PS1 or APP and found that N-terminally truncated Aβ was overrepresented in Alzheimer's brains. Examples of N terminally truncated Aβ include those described by Russo.

The term "Aβ derived peptides" as used herein is defined as encompassing Aβ and N terminal truncated Aβ. The term "Aβ derived peptide" therefore encompasses $A\beta_{x-38}$, $A\beta_{x-39}$, $A\beta_{x-40}$, $A\beta_{x-41}$, $A\beta_{x-42}$, and $A\beta_{x-43}$ where "x" is defined as equal to 1 and less than or equal to 22.

The term "β-amyloid precursor protein" (APP) as used herein is defined as a polypeptide that is encoded by a gene of the same name localized in humans on the long arm of chromosome 21 and that includes Aβ (see above), within its carboxyl third. APP is a glycosylated, single-membrane spanning protein expressed in a wide variety of cells in many mammalian tissues. Examples of specific isotypes of APP which are currently known to exist in humans are the 695 amino acid polypeptide described by Kang et. al. (1987) *Nature* 325:733–736 which is designated as the "normal" APP The 751 amino acid polypeptide described by Ponte et al. (1988) *Nature* 331:525–527 (1988) and Tanzi et al. (1988) *Nature* 331:528–530 and the 770-amino acid polypeptide described by Kitaguchi et. al. (1988) Nature 331:530–532. Examples of specific variants of APP include point mutations which can differ in both position and phenotype (for review of known variant mutation see Hardy (1992) Nature Genet. 1:233–234). In three APP mutants, valine-642 in the transmembrane domain of APP(695) is replaced by isoleucine, phenylalanine, or glycine in association with dominantly inherited familial Alzheimer disease. (According to an earlier numbering system, val642 was numbered 717 and the 3 mutations were V717I, V717F, and V717G, respectively.) Yamatsuji et al. ((1996) Science 272:1349–1352) concluded that these three mutations account for most, if not all, of the chromosome 21-linked Alzheimer disease. Suzuki et al. ((1994) Science 264:1336–1340) suggested that these mutations may cause Alzheimer disease by altering APP processing in a way that is amyloidogenic. They found that the APP-717 mutations were consistently associated with a 1.5- to 1.0-fold increase in the percentage of longer Aβ generated and that the longer species formed insoluble amyloid fibrils more rapidly than did the shorter ones. In transgenic mice, overexpression of such mutants mimics the neuropathology of AD. The term "APP" encompasses fragments of APP other than those which consist solely of Aβ or N terminally truncated Aβ.

The term "APP processing" refers to proteolytic cleavage of the APP molecule. APP processing is subject to intervention and may be "modified.

The term "modulate Aβ derived peptide production" means to change the amount of any Aβ derived peptide produced. It will be appreciated that this definition also includes changing the relative proportion of individual species of Aβ derived peptides one to another. By way of non limiting example therefore, a test agent which increases the ratio of $A\beta_{1-40}/(A\beta_{1-40}+A\beta_{1-42})$ would be said to be an "agent which modulates Aβ derived peptide production" as would an agent which reduces the levels of $A\beta_{1-40}$ and $A\beta_{1-42}$ each to the same extent would be "agent which modulates Aβ derived peptide production".

Polypeptides of the Invention

Polypeptides of the present invention are mutants of the presenilin polypeptides (mutant PS1 polypeptide or mutant PS2 polypeptide). They are of interest because they are involved in the processing of amyloid precursor protein (APP) from which the major amylodogenic peptides $A\beta_{1-40}$ or $A\beta_{1-42}$ are cleaved. The cleavage of Aβ from APP is accomplished by the action of two proteolytic activities commonly denoted as beta-secretase and gamma-secretase. The most common cause of familial Alzheimer's disease (FAD) are mutations found in the coding regions of the genes encoding presenilins 1 and 2 (hereinafter PS1 and PS2). The clinical mutations all cause at least one phenotypic alteration: increase in the production of $A\beta_{1-42}$ from cells secreting the amyloid precursor protein (APP). Deletion of the PS1 gene in mice greatly reduces gamma-secretase activity.

Recently it has been reported that the aspartic acid residues (D) found at positions 257 and 385 in PS1 and the homologous aspartic acid residues found at positions 263 and 366 in PS2 are necessary for gamma-secretase activity since changing these aspartic acid residues to either alanine or glutamic acid residues abrogates production of Aβ in stably transfected cell lines carrying both mutated PS1 and PS2 (PS1m and PS2m) cDNAs. These observations suggest that there may be some intrinsic activity related to the transmembrane 6 and 7 aspartic acid residues which influences APP processing.

The sequence following the D at amino acid position 257 in wild type PS1 is —LV (at amino acid positions 258 and 259). The sequence found after the D at amino position 385 in the wild type PS1 is —FI— (at amino acid positions 386 and 387).

The situation with PS2 is analogous. The sequence following the D at 263 in wild type PS2 is —LV (at amino acid positions 264 and 265). The sequence following the D at 366 in wild type PS2 is —FI (at amino acid positions 367 and 368).

Without intending in any way to be bound by theory, it is postulated that the wild type sequences provide some minimal level of proteolytic activity with APP or gamma secretase as substrate to provide a phenotypic effect. The present invention optimizes the proteolytic activity so as to make possible an efficient assay for inhibitors of PS1 and PS2 activity.

Single Partial and Single Complete Canonical Mutants of the Invention

The present invention provides mutant PS1 polypeptides and nucleic acids encoding them which have a threonine and conservative substitutions of threonine at the position directly adjacent to either putative canonical aspartic residues and/or a glycine at the amino acid position one amino acid removed from either canonical aspartate.

The present invention then, provides either "single partial canonical mutants" of PS1 (DLG, DTV, at 257–259 and DFG, DTI at 385–387) or "single complete canonical mutants" (DTG at positions 257–259 or 385–387). If conservative amino acid substitutions are introduced for T or G the mutants are designated "substituted single partial canonical mutants" or "substituted single complete canonical mutants" respectively. By way of example, a single mutant PS1, mutated at 258–259 to encode DLG would be designated 'PS1-DLG/wt" and would be described as a "single partial canonical mutant". By way of further example a single mutant PS1 mutated at 258–259 to encode DTG at that positions would be designated PS1-DTG/wt and would be described as a "single complete canonical mutant"

The present invention also provides mutant PS2 polypeptides and nucleic acids encoding them which have a threonine and conservative substitutions of threonine at the position directly adjacent to either putative canonical aspartic residues and/or a glycine at the amino acid position one amino acid removed from either canonical aspartate.

The present invention then, provides either "single partial canonical mutants" of PS2 (DLG, DTV, at 263–265 and DFG, DTI at 366–368) or "single complete canonical mutants" (DTG at positions 263–265 or 366–368). If conservative amino acid substitutions are introduced for T or G the mutants are designated "substituted single partial canonical mutants" or "substituted single complete canonical mutants" respectively. By way of example, a single mutant PS2, mutated at 264–265 to encode DLG would be designated 'PS1-DLG/wt" and would be described as a "single partial canonical mutant". By way of further example a single mutant PS2 mutated at 264–265 to encode DTG at that positions would be designated PS1-DTG/wt and would be described as a "single complete canonical mutant".

Double Partial and Double Complete Canonical Site Mutants of the Invention

The present invention provides mutant PS1 polypeptides and nucleic acids encoding them which have a threonine and conservative substitutions of threonine at the position directly adjacent to both putative canonical aspartic residues and/or a glycine at the amino acid position one amino acid removed from both canonical aspartate.

The present invention then, provides either "double partial canonical mutants" of PS1 (DLG, DTV, at 257–259 and DFG, DTI at 385–387) or "double complete canonical mutants" (DTG at positions 257–259 or 385–387). If conservative amino acid substitutions are introduced for T or G the mutants are designated "substituted double partial canonical mutants" or "substituted double complete canonical mutants" respectively. By way of example, a double mutant PS1, mutated at 258–259 and 385–387 to encode DLG would be designated 'PS 1-DLG/DLG" and would be described as a "double partial canonical mutant". By way of further example a double mutant PS1 mutated at 258–259 and 385–387 to encode DTG at both positions would be designated PS1-DTG/DTG and would be described as a "double complete canonical mutant"

The present invention also provides mutant PS2 polypeptides and nucleic acids encoding them which have a threonine and conservative substitutions of threonine at the position directly adjacent to either putative canonical aspartic residues and/or a glycine at the amino acid position one amino acid removed from either canonical aspartate.

The present invention then, provides either "double partial canonical mutants" of PS2 (DLG, DTV, at 263–265 and DFG, DTI at 366–368) or "double complete canonical mutants" (DTG at positions 263–265 or 366–368). If conservative amino acid substitutions are introduced for T or G the mutants are designated "substituted double partial canonical mutants" or "substituted double complete canonical mutants" respectively. By way of example, a double mutant PS2, mutated at 264–265 to encode DLG would be designated 'PS1-DLG/wt" and would be described as a "single partial canonical mutant". By way of further example a single mutant PS2 mutated at 264–265 and 367–368 to encode DTG at both positions would be designated PS2-DTG/DTG and would be described as a "double complete canonical mutant".

These —TG-and conservative variant substitutions in both PS1 and PS2 particularly the double mutants have a robust effect on $A\beta_{1-42}$ but not $A\beta_{1-40}$ production in the cell lines transfected. As such the polypeptides of the present invention would be useful to identify test agents which might inhibit their enhanced activity and thereby identify chemical structures which would be useful to inhibit the native activity of PS1 or PS2 in screens. The enhanced activity of the polypeptides of the present invention also provide a robust assay for candidate compound inhibitors of the native activity of the PS1 and PS2 polypeptides.

The Polynucleotides of the Invention

As is well known in the art, due to the degeneracy of the genetic code, there are numerous other DNA and RNA molecules that can code for the same polypeptide as that encoded by the aforementioned mutant PS1 and PS2 polypeptides. The present invention, therefore, contemplates those other DNA and RNA molecules which, on expression, encode the polypeptides of SEQ ID NOS: 4–6 and 10–12. Having identified the amino acid residue sequence encoded by a mutant PS1 or PS2 polypeptide, and with the knowledge of all triplet codons for each particular amino acid residue, it is possible to describe all such encoding RNA and DNA sequences. DNA and RNA molecules other than those specifically disclosed herein characterized simply by a change in a codon for a particular amino acid, are, therefore, within the scope of this invention.

A table of amino acids and their representative abbreviations, symbols and codons is set forth below in the following Table 1.

| Amino acid | Abbrev. | Symbol | Codon(s) | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |

-continued

| Amino acid | Abbrev. | Symbol | | Codon(s) | | | | |
|---|---|---|---|---|---|---|---|---|
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

As is well known in the art, codons constitute triplet sequences of nucleotides in mRNA and their corresponding cDNA molecules Codons are characterized by the base uracil (U) when present in a mRNA molecule but are characterized by base thymidine (T) when present in DNA. A simple change in a codon for the same amino acid residue within a polynucleotide will not change the sequence or structure of the encoded polypeptide., It is apparent that when a phrase stating that a particular 3 nucleotide sequence "encode(s)" any particular amino acid, the ordinarily skilled artisan would recognize that the table above provides a means of identifying the particular nucleotides at issue. By way of example, if a particular three nucleotide sequence encodes theonine the table above discloses that the possible triplet sequences are ACA, ACG, ACC and ACU (ACT if in DNA).

The construction of representative mutant PS1 and PS2 polynucleotide sequences is demonstrated in the following example. By way of illustrative example.

EXAMPLE 1

The objective of this experiment was to introduce aspartyl protease consensus sequence motifs at the adjacent to the aspartic acid residues within transmembrane 6 and 7 of PS1 and PS2 so that the effects on APP processing could be accessed.

Generation of Aspartyl Acid Concensus Sequence Sites in PS1 and PS2

Wild-type presenilin 1 and 2 cDNAs were cloned into the Invitrogen plasmids pcDNA3.1 Hyg(−) and pcDNA3.1 Zeo (+) vectors respectively. These plasmids were mutated at positions 258 (L->T), 259 (V->G), 386 (F->T), 387 (I->G) in PS1 and 264 (L->T), 265 (V->G), 367 (F->T), 368 (I->G) in PS2. The procedure was carried out using a Stratagene QuikChange ™ Site-Directed Mutagenesis kit with the following conditions: PCR cycling;

Segment 1, 95 deg. 30 seconds; Segment 2, 18 cycles at 95 deg. 30 seconds, 55deg. 1 minute, 68 deg. 3 minutes. The oligos used were

```
for PS1:
SEQ ID NO:13 = 5' GCT GTG ATT TCA GTA TAT GAT ACA GGG GCT GTT TTG TGT CCG AAA GG 3'

SEQ ID NO:14 = 5' CC TTT CGG ACA CAA AAC AGG CCC TGT ATC ATA TAC TGA AAT CAC AGC 3'

SEQ ID NO:15 = 5' G GGA GTA AAA CTT GGA TTG GGA GAT ACC GGT TTC TAC AGT GTT CTG G 3'

SEQ ID NO:16 = 5' C CAG AAC ACT GTA GAA ACC GGT ATC TCC CAA TCC AAG TTT TAC TCG C 3' and for PS2:
SEQ ID NO:17 = 5' G GGC GGG ATC TCT GTG TAT GAT ACC GGG GCT GTG CTG TGT CC 3'

SEQ ID NO:18 = 5' GG ACA CAG CAC AGC CCC GGT ATC ATA CAC AGA GAT GGC GCC G 3'

SEQ ID NO:19 = 5' G CTT GGC CTC GGG GAC ACC GGC TTC TAC AGT GTG CTG GTG G 3'

SEQ ID NO:20 = 5' C CAC CAG CAC ACT GTA GAA GCC GGT GTG CCC GAG GCC AAG C 3'.
```

Candidate clones were derived and sequenced. Clones having the desired mutations at the positions denoted above were grown for preparation of milligram quantities of plasmid.

Production of the Polypeptides of the Invention

Having constructed mutant polynucleotides encoding mutant PS1 and PS2 polypeptides, the ability to produce the mutant polypeptides is apparent. Expression constructs are preferably utilized for production of an encoded protein, but also may be utilized simply to amplify a mutant PS1 or PS2 encoding polynucleotide sequence.

According to another aspect of the invention, host cells are provided, including prokaryotic and eukaryotic cells, comprising a polynucleotide of the invention (or vector of the invention) in a manner, which permits expression of the encoded mutant PS1 or PS2 polypeptide. Polynucleotides of the invention may be introduced into the host cell as part of a circular plasmid, or as linear DNA comprising an isolated protein coding region or a viral vector. Methods for introducing DNA into the host cell well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, and mammalian cells systems.

Host cells for expression of mutant PS1 or PS2 polypeptides include prokaryotes, yeast, and higher eukaryotic cells. Suitable prokaryotic hosts to be used for the expression of mutant PS1 or PS2 polypeptides include but are not limited to bacteria of the genera Escherichia, Bacillus, and Salmonella, as well as members of the genera Pseudomonas, Streptomyces, and Staphylococcus.

The isolated nucleic acid molecules of the invention are preferably cloned into a vector designed for expression in eukaryotic cells, rather than into a vector designed for expression in prokaryotic cells. Eukaryotic cells are preferred for expression of genes obtained from higher eukaryotes because the signals for synthesis, processing, and secretion of these proteins are usually recognized, whereas this is often not true for prokaryotic hosts (Ausubel, et al., ed., in Short Protocols in Molecular Biology, 2nd edition, John Wiley & Sons, publishers, pg. 16–49, 1992.). Eukaryotic hosts may include, but are not limited to, the following: insect cells, African green monkey kidney cells (COS cells), Chinese hamster ovary cells (CHO cells), human 293 cells, human SH-EP1 cells and murine 3T3 fibroblasts.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

The mutant PS1 or PS2 polypeptides may also be expressed in yeast host cells from genera including Saccharomyces, Pichia, and Kluveromyces. Preferred yeast hosts are *S. cerevisiae* and *P. pastoris*. Yeast vectors will often contain an origin of replication sequence from a 2 micron yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*.

Insect host cell culture systems may also be used for the expression of mutant PS1 or PS2 polypeptides. In a preferred embodiment, the mutant PS1 or PS2 polypeptides of the invention are expressed using a baculovirus expression system. Further information regarding the use of baculovirus systems for the expression of heterologous proteins in insect cells are reviewed by Luckow and Summers, *Bio/Technology* 6:47 (1988).

In another preferred embodiment, the mutant PS1 or PS2 polypeptide is expressed in mammalian host cells. Non-limiting examples of suitable mammalian cell lines include the COS-7 line of monkey kidney cells (Gluzman et al., *Cell* 23:175 (1981)), Chinese hamster ovary (CHO) cells, and human 293 cells.

The choice of a suitable expression vector for expression of the mutant PS1 or PS2 polypeptide of the invention will of course depend upon the specific host cell to be used, and is within the skill of the ordinary artisan. Examples of suitable expression vectors include pcDNA3 (Invitrogen) and pSVL (Pharmacia Biotech). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO91/18982.

EXAMPLE 2
Transient Transfections of Mutant Constructs

The construction of the cell lines used in this section has been described in U.S. Pat. No. 6,440,698. Transient transfections were carried out in 4 different cell lines: H125.3-16, N2A-APP, H143.3-23, and H167-11. The H125.3-16 cell line expresses human APP695 swedish mutant cDNA with a dilyine motif in HEK-293 cells, and the H 143.3-23 cell line expresses human APP695 swedish mutant cDNA in HEK-293 cells. The H167-1 1 cell line was developed using the same methods as the H125.3-16 and H143.3-23 cell lines, except the 167 construct DNA (pTRES-EGFP harboring the human APP695 V642F mutant cDNA containing a dilyine motif) was used. The 167 DNA construct was made by performing site-directed mutagenesis on the 142.3 construct (pIRES-EGFP harboring human APP695 with dilyine motif, using the Stratagene Quik-Change site-directed mutagenesis kit with the following oligonucleotides ALZ-111 5'GCG ACA GTG ATC tTC ATC ACC TTG GTG 3' (SEG ID NO. 21) and ALZ-112 5' CAC CAA GGT GAT GAa GAT CAC TGT CGC 3' (SEQ ID NO. 22) to introduce the V642F FAD mutation. The N2A-APP cell line expresses human APP695 swedish mutant with a dilyine motif in a Neura-2A mouse neuroblastoma cell line.

Transient Transfection Procedures

Twenty-four hours prior to transfection, cells were plated at $6 \times 10^5$ cells per well of a six-well dish. For each well of the six-well dish, 2 µg plasmid DNA was combined with 10 µl lipofectamine (Gibco BRL) in 200 µl OptiMEM media; the mixture was incubated at room temperature for 45 minutes. Then 800 µl OptiMEM was added to the DNA/lipid mixture. The cells were washed once with OptiMEM media and the 1 ml DNA/lipid mixture was placed on the cells and incubated at 37° C., 5% $CO_2$, for 5 hours. The DNA/lipid/media mixture was aspirated and the cells were fed with complete media. Complete media for the HEK-293 APP stable cell line is DMEM containing 10% fetal bovine serum, 100 U/ml penicillin, 100 µg/ml streptomycin, 1 mM sodium pyruvate, and 400 µg/ml G418. Complete media for the N2A-APP stable cell line is MEM containing 10% fetal bovine serum, 100 U/ml penicillin, 100 µg/ml streptomycin, 2 mM glutamine, 1 mM sodium pyruvate, 0.1 mM non-essential amino acids, and 400 µg/ml G418. Conditioned media was collected from the cells 48 hours after transfection and then analyzed by Elisa assay for levels of $A\beta_{1-40}$ and $A\beta_{1-42}$. The results are discussed in Example 3.

It is to be recognized that polypeptides of the invention may be produced by natural cell sources or may be chemically synthesized, but are preferably produced by recombinant procedures involving host cells of the invention. Use of mammalian host cells is expected to provide for such post-translational modifications (e.g., glycosylation, truncation, lipidation, and phosphorylation) as may be needed to confer optimal biological activity on recombinant expression products of the invention. Glycosylated and non-glycosylated forms mutant PS1 or PS2 polypeptides are embraced.

The invention also embraces allelic variants of mutant PS1 or PS2 polypeptides wherein the enhanced protease activity of the mutant PS1 or PS2 polypeptides is maintained. Examples of such variants include insertion, deletions or substitutions. Insertional variants also include fusion proteins wherein the amino and/or carboxy termini of the mutant PS1 and PS2 polypeptides. It is further envisioned that the although the polypeptides of the invention disclosed in SEQ ID NOS: 4, 5, 6, 10, 11, and 12, and 14, contain transmembrane sequences necessary for insertion into the cell membrane, the invention also includes polypeptides with the transmembrane sequences removed.

In another aspect, the invention provides deletion variants wherein one or more amino acid residues in a mutant PS1 or PS2 polypeptides are removed. Deletions can be effected at one or both termini of the mutant PS1 or PS2 polypeptides or with removal of one or more residues within the mutant PS1 or PS2 polypeptide amino acid sequence.

In still another aspect, the invention provides substitution variants mutant PS1 or PS2. Substitution variants include those polypeptides wherein one or more amino acid residues of a mutant PS1 or PS2 polypeptides are removed and replaced with alternative residues. In one aspect, the substitutions are conservative in nature, however, the invention embraces substitutions that are also non-conservative. Conservative substitutions for this purpose may be defined as set out in Tables A, B, or C below.

Variant polypeptides include those wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (from WO 97/09433, page 10, published Mar. 13, 1997 (PCT/GB96/02197, filed Sep. 6, 1996), immediately below.

TABLE A

Conservative Substitutions I

| SIDE CHAIN CHARACTERISTIC | AMINO ACID |
|---|---|
| Aliphatic | |
| Non-polar | G A P |
| | I L V |
| Polar - uncharged | C S T M |
| | N Q |
| Polar - charged | D E |
| | K R |
| Aromatic | H F W Y |
| Other | N Q D E |

Alternatively, conservative amino acids can be grouped as described in Lehninger, [Biochemistry, Second Edition; Worth Publishers, Inc. N.Y.: N.Y. (1975), pp. 71–77] as set out in Table B, immediately below

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |

TABLE B-continued

Conservative Substitutions II

| SIDE CHAIN CHARACTERISTIC | AMINO ACID |
|---|---|
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still an another alternative, exemplary conservative substitutions are set out in Table C, immediately below.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr |
| Tyr (Y) | Trp, Phe, Thr, Ser |
| Val (V) | Ile, Leu, Met, Phe, Ala |

The invention also conveys the methods for using the novel constructs to identify compounds which will be useful in treating the following pathologies: Alzheimer's disease, Parkinson's disease, multiple sclerosis, Huntington's disease, amylotrophic lateral sclerosis, head injury damage, Picks Disease, frontal lobe dementia, cerebellar degeneration, ischemia reperfusion injury, stroke, ischemic injury and schizophrenia, hereinafter referred to as "the Diseases". The invention relates to methods provided by the invention for identifying agonist, antagonists or inhibitors of activity intrinsic to wild-type PS1 or PS2. Various assays are described hereinafter.

EXAMPLE 3

Effect of Mutant PS1 and PS2 Polypeptides on APP Processing

Three cell lines were used for these experiments, HEK cells stably transfected with the APP695sw-KK cDNA (H125.3-16) to produce moderate levels of Aβ, HEK cells stably transfected with APP695sw without the dilysine motif (H143.3-23) and HEK cells stably transfected with APP695V642F-KK (H167-11). Analysis of conditioned media (CM) 48 hours after transfection show the following results. The values of Aβ for mock (pcDNA vector) transfected cells for each stable cell line were used as a reference for the % change Aβ values obtained after transfection with the various plasmids. When the H125.3 or H143.3-23 cells were transfected with BACE alone (Asp2), there was always a robust increase in both $A\beta_{1-40}$ and $A\beta_{1-42}$ peptides in the CM. However wild-type PS1 (PS1 wt) or PS1 (D257A) had a slight lowering effect on Aβ production. Transfection of the H125.3 or the H143.3 cell lines with the doubly mutated PS1 -DTG/DTG caused a substantial increase in $A\beta_{1-42}$ but not $A\beta_{1-40}$ production. The increase in $A\beta_{1-42}$ caused by transfection with PS1-DTG/DTG was not increased further by co-transfection with As constructs were also carried out in a cell line carrying the APP695-V642F mutant cDNA with a dilyine motif (H167-11) The V642 F mutation is located at the C-terminus of Aβ. Only transfection with the Asp2 plasmid caused an increase as compared to the mock-transfected values of $A\beta_{1-40}$ or $A\beta_{1-42}$ in the H 167-11 cell line.

In a second experiment, similar results were obtained for the PS2-DTG/DTG construct when it was transfected into the H125.3-16 or the H167-11 cell lines. Transfection with PS2-DTG/DTG increased $A\beta_{1-42}$ levels but not $A\beta_{1-40}$ levels in the H125.3-16 cell line, while both $A\beta_{1-40}$ and $A\beta_{1-42}$ did not increase in the H167-11 cell line following transfection with PS2-DTG/DTG. The increases in $A\beta_{1-42}$ production for the PS2-DTG/DTG plasmid were not as robust as those illicited by the PS1-DTG/DTG plasmid. Also there was no detectable synergism between the DTG/DTG PS1 and PS2 mutants. The increase in $A\beta_{1-42}$ caused by transfection with PS2-DTG/DTG was not increased further by co-transfection with Asp2.

In a third independent experiment, a PS1 construct having the —TG-substitution only at the 386 and 387 positions (within transmembrane 7) was compared to the PS1-DTG/DTG, PS1-M146V and PS1-C410Y constructs. The latter two PS1 constructs replicate the clinical mutations found to cause early onset FAD. $A\beta_{1-42}$ production is increased in CM from fibroblasts taken from patients having the M146V and C410Y mutations (1). The introduction of the single —TG-mutation following the aspartic acid residue in TM 7 of PS1 appears to have a similar effect on $A\beta_{1-42}$ production as the double DTG substitution in both the H125.3 cells as well as the mouse neuroblastoma Neuro 2A cells stably transfected with APP695sw-KK. The —TG-substitution is substantially more effective at increasing Aβ42 production than the clinical mutations examined. The ratio of the PS1-DTG/DTG $A_{1-42}$ to the PS1-M146V $A\beta_{1-42}$ is roughly 5:1, whereas for the Δ9 to the M146V mutations the ratio is 2:1 (1). The Δ9 mutation is a very efficacious clinical mutant in increasing $A\beta_{1-42}$.

Soluble APP levels were also measured by Elisa assay for conditioned media from all PS1 and PS2 DTG/DTG transfection experiments; however, no consistent, definitive changes in sAPP levels were detected.

In summary the introduction of a consensus aspartyl protease domain 3' to the TM6 and 7 aspartic acid residues of PS1 or PS2 robustly increases $A\beta_{1-42}$ production in neuronal and non-neuronal cell lines whereas $A\beta_{1-40}$ is unchanged.

In Vitro—Secretase Assay

Another aspect of the present invention is directed to methods of identifying test agents which modulate activity of an isolated mutant presenilin comprising contacting an PS1 or PS2 polypeptide with a test compound, and determining whether the compound modifies activity of the PS1 or PS2 polypeptide. The activity of the polypeptide in the presence of the test compound is compared to the activity in the absence of the test compound. Where the activity of the sample containing the test compound is higher than the activity in the sample lacking the test compound, the compound will have increased activity of the polypeptide. Similarly, where the activity of the sample containing the test compound is lower than the activity in the sample lacking the test compound, the compound will have inhibited the activity of the polypeptide. Such compounds are inhibitors of the invention.

An inhibitor of the invention as measured either in a cell based or in-vitro assay either inhibits the production of $A\beta_{1-40}$ or A-beta$_{1-42}$ altogether or alters the ratio $A\beta_{1-40}/A\beta_{1-40}+A\beta_{1-42}$ (in these assays, or in cell extracts or after release into the medium in cell based assays by ELISA or other assays which are known in the art (Borchelt et al., Neuron 17: 1005–1013 (1996); Citron et al., Nat. Med. 3: 67–72 (1997)).

The inhibitors of the invention exhibit a variety of chemical structures, which can be generally grouped into peptide and non-peptide inhibitors, The invention does not restrict the sources for suitable inhibitors, which may be obtained from natural sources such as plant, animal or mineral extracts, or non-natural sources such as small molecule libraries, including the products of combinatorial chemical approaches to library construction, and peptide libraries.

EXAMPLE 4

Membrane Preparation and Detergent Solubilization (Polypeptide Isolation)

HEK293 cells stably transfected with a nucleic acid encoding mutant PS1 or PS2 are grown in bioreactors (Analytical Biological Services, Wilmington, Del.) in 90% DMEM, 10% FBS, 2 mM glutamine, and 100 μg/ml each of penicillin and streptomycin. Frozen cells are resuspended in buffer A (50 mM Mes, pH 6.0/5 mM $MgCl_2$/5 mM $CaCl_2$/150 mM KCl) containing complete protease inhibitor mixture (Boehringer Mannheim). The cells are broken by single-pass through a French press (Spectronic Instruments, Rochester, N.Y.). Cell debris and nuclei are removed by centrifugation at 800×g for 10 min. The supernatant solutions are centrifuged at 100,000×g for 60 min. The ensuing pellets are resuspended in buffer A, and the centrifugation was repeated. The final membrane pellets are resuspended in buffer A to yield a protein concentration of approximately 12 mg/ml. All procedures are performed at 4° C. The membranes are stored at −70° C. Detergent solubilization of HEK-mutant PS1 or PS2 cell membranes (protein concentration, 2.5 mg/ml in buffer A) involves treatment with 1% CHAPSO (3-[(3-cholamidopropyl) dimethylammonio]-2-hydroxy-1-propanesulfonate) for 60 min at 4° C. and centrifugation at 100,000×g for 60 min. The ensuing supernatant solution is designated "solubilized-secretase"

In Vitro—Secretase Assay

A DNA fragment encoding amino acids 596–695 of the 695-aa isoform of APP (APP695) and the Flag sequence (DYKDDDDK) at the C terminus are generated by PCR amplification with suitably designed oligonucleotides and the APP695 cDNA. The Met that serves as the translation start site is residue 596 of APP695 (the P1 residue with respect to the -secretase cleavage site). This DNA fragment is then inserted into the prokaryotic expression vector pET2-21b (Novagen). The recombinant protein, C100Flag, is overproduced in *Escherichia coli* [strain BL21(DE3)] and purified by Mono-Q column chromatography (Amersham Pharmacia Biotech). C100flag (1.7 μM) is incubated with cell membranes (0.5 mg/ml) in the presence of CHAPSO, CHAPS (3-[(3-cholamidopropyl)dimethylammonio]-1-propanesulfonate), or Triton X-100 (0, 0.125, 0.25, 0.5, or 1%) in buffer B (50 mM Pipes, pH 7.0/5 mM MgCl$_2$/5 mM CaCl$_2$/150 mM KCl) at 37° C. The reactions were stopped by adding RIPA (150 mM NaCl/1.0% NP-40/0.5% sodium deoxycholate/0.1% SDS/50 mM Tris HCl, pH 8.0) and boiling for 5 min. The samples are centrifuged and the supernatant solutions is assayed for the A peptides by ECL. The A40- and A42-related products from -secretase-mediated processing of C100Flag possess a Met at the N terminus and are thus defined as M-A40 and M-A42, respectively. Likewise, supernatant solution (0.125 mg/ml) from CHAPSO-extracted HEK293-PS1-DTG/DTG cell membranes (solubilized-secretase) is incubated with C100Flag (1.7 $\mu$M) in buffer B containing 0.25% CHAPSO and subsequently assayed for M-A40 and M-A42 by using ECL. Test agents which inhibit secretase activity are drug candidates.

EXAMPLE 5

Inhibition Assay—Stable Cell Lines

The purpose of the experiment was to assess the effect of compounds known or postulated to have an effect on processing at the proposed gamma cleavage site Methods The compounds used were L685,458 (Bachem Cat # H-5106) described by Li et al (15), one we have designated 512088, a fenchylamine sulfonamide inhibitor described by Rishton et al. (16). Z-Leu-Leu-Leu-H, also known as MG132 (Peptide Institute Cat # 3175-v) described by Tajima et al (17), and DMSO (Aldrich Cat # 27,685-5) as a vehicle control. All drugs were resuspended in DMSO at a concentration of 10 mM. Serial dilutions of the drugs were made in cell culture media [DMEM (Gibco cat # 11965-092) supplemented with 10% fetal bovine serum, 1 mM sodium pyruvate, 100 units/ml penicillin G, 100 ug/ml streptomycin sulfate, and 400 ug/ml Geneticin]. Stable cell lines used for drug testing were H125.3-16 (expressing APP-Sw-KK), APA2 (co-expressing APP-Sw-KK and PS1-wt), APB10 (co-expressing APP-Sw-KK and PS1-DTG385), and APD3 (co-expressing APP-Sw-KK and PS1-M146V). APP-Sw-KK (An APP construct with a di-lysine motif at the C terminus) has been described in U.S. patent application Ser. No. 09/416901 filed Oct. 13, 1999 and also in WO 00/17369 "Alzheimer's Disease Secretase" published Mar. 30, 2000. Cells were plated at a concentration of 2.5×10$^4$ or 5.0×10$^4$ cells per well of a 96 well dish on day 1. Cells were treated with various concentrations of drugs on day 3. Conditioned media was harvested 24 hours post-treatment and analyzed in an Elisa assay for A$\beta$40 or A$\beta$42 levels (Described below). An MTS assay (Promega) was performed on the cells 24 hours post-treatment to assess toxicity levels of the drugs.

ELISA Procedure Materials

Primary Antibody 6E10 was purchased from Senetek PLC (St. Louis, Mo.). Secondary Antibodies 162, 163, 164 and 165 were purchased from New York Institute for Basic Research (Staten Island, N.Y.). $\beta$ Bachem (Torrence, Calif.). $\beta$-Amyloid 1-40 is cat #ZN571) and 1-42 is cat #ZN327) Neutravidin was purchased from Pierce (Rockford, Ill.). The tetramethylbenzidine color development system was purchased from Kirkigaard & Perry Laboratories Inc. (Gaithersburg, Md.). Plates were read on a Molecular Devices Thermomax Plate Reader with integrated software that calculated the data and analyzed confidence values for the samples.

The coating buffer is 0.1M NaHCO$_3$, pH8.2. Wash buffer is Dulbecco's PBS+0.05% Tween 20 (PBST). Blocking buffer is PBST+1% BSA (make up fresh the day of assay). The substrate is TMB Kirkegaard & Perry Labs. (cat.no.50-76-03). Plates are Costar 96 well half area EIA plates (cat.no.3690). Supplemental BSA is supplied as PBST+10% BSA made fresh on the day of assay.

Procedure

1. Coat half area 96 well plates (Costar 3690) overnight @ 4° C. with capture antibody 6E10 (50 $\mu$l/well) made at 4 $\mu$l/ml in coating buffer, pH8.2.
2. Wash plates on an automatic plate washer 1× with wash buffer (175 $\mu$l/well).
3. Add 75 ul of blocking buffer to each well. Incubate 1 hr. @room temperature, then wash 3×.
4. Make standard curves from fresh aliquots for each amyloid in blocking buffer as follows:

(note: standards should be made in the solvent that the samples are in especially if it is different than the blocking buffer and it affects the standard curve)

a. A$\beta$ 1-40 (10 $\mu$M stock in DMSO): Make an initial dilution of 2:108 in blocking buffer, then dilute that solution 1:100 to get the 8000 pg/ml initial standard. Make ten 1:2 serial dilutions from the initial 8000 pg/ml standard and add a tube of buffer only to get a final standard curve of:
   0, 8, 16, 32, 63, 125, 250, 500, 1000, 2000, 4000, 8000 pg/ml.
   b. A$\beta$ 1-42 (10 $\mu$M. stock in DMSO): Make an initial dilution of 2:113 then follow the instructions for Abeta 1-40 starting at the 1:100 dilution.

5. Add 50 $\mu$l of each std. (use duplicates) or sample dilution into the appropriate wells.

Incubate the standards and unknown samples @ room temperature for 3 to 4 hrs. If the samples being assayed contain no protein, 5 $\mu$l. of supplemental 10% BSA should be added to the sample wells before adding 50 $\mu$l. of sample.

6. Dilute biotin-labelled anti-A$\beta$ antibodies in blocking buffer as follows:
   a. Antibody 162 1:2000 (abeta 1-40)
   b. Antibody 164 1:200 (abeta 1-42)
   c. Antibody 165 1:1000 (abeta 1-42)
7. Wash plates 3× then add 50 ul /well of the appropriate bioatinylated secondary antibody from step 6 and incubate 1 hr @ room temperature.
8. Dilute Neutravidin (Pierce Chem. Co.) 1:5,000 in blocking buffer.
9. Wash plates 3× then add 50 ul/well of the Neutravidin and incubate 30 min. @ r.t.
10. Mix equal volumes of the two TMB solutions (Kirkegaard & Perry).
11. Wash the plates 3× then add 50 ul/well of the TMB solution and incubate 1 hr @r.t.
12. Stop the color development by adding 50 ul/well 1M phosphoric acid.
13. Read O.D. 450 on a microtiter plate reader.

Unknowns are read against the standard curve; calculated using 4-par logistics

Results

Three stable cell lines were investigated for the ability of known gamma-secretase inhibtors (512088, L685,458) as well as proteasome inhibitors (MG132, lactacystin) and Pepstatin to inhibit secretion of A$\beta_{1-40}$ and A$\beta_{1-42}$ production. H125.3-16 cell line is a cell line stably expressing a version of the APPsw-kk construct, APA2 coexpresses APPsw-kk and PS1wt and APB10 coexpresses APPsw-kk and PS1-DTG385. The objective of the experiments was to see if the dose response profile in the 2 cases where a native PS1 was active (H125.3-16, APA2) were different from the dose response profile of a cell line in which the primary contribution came from the action of the PS1-DTG385 version of PS1.

Figure 4:
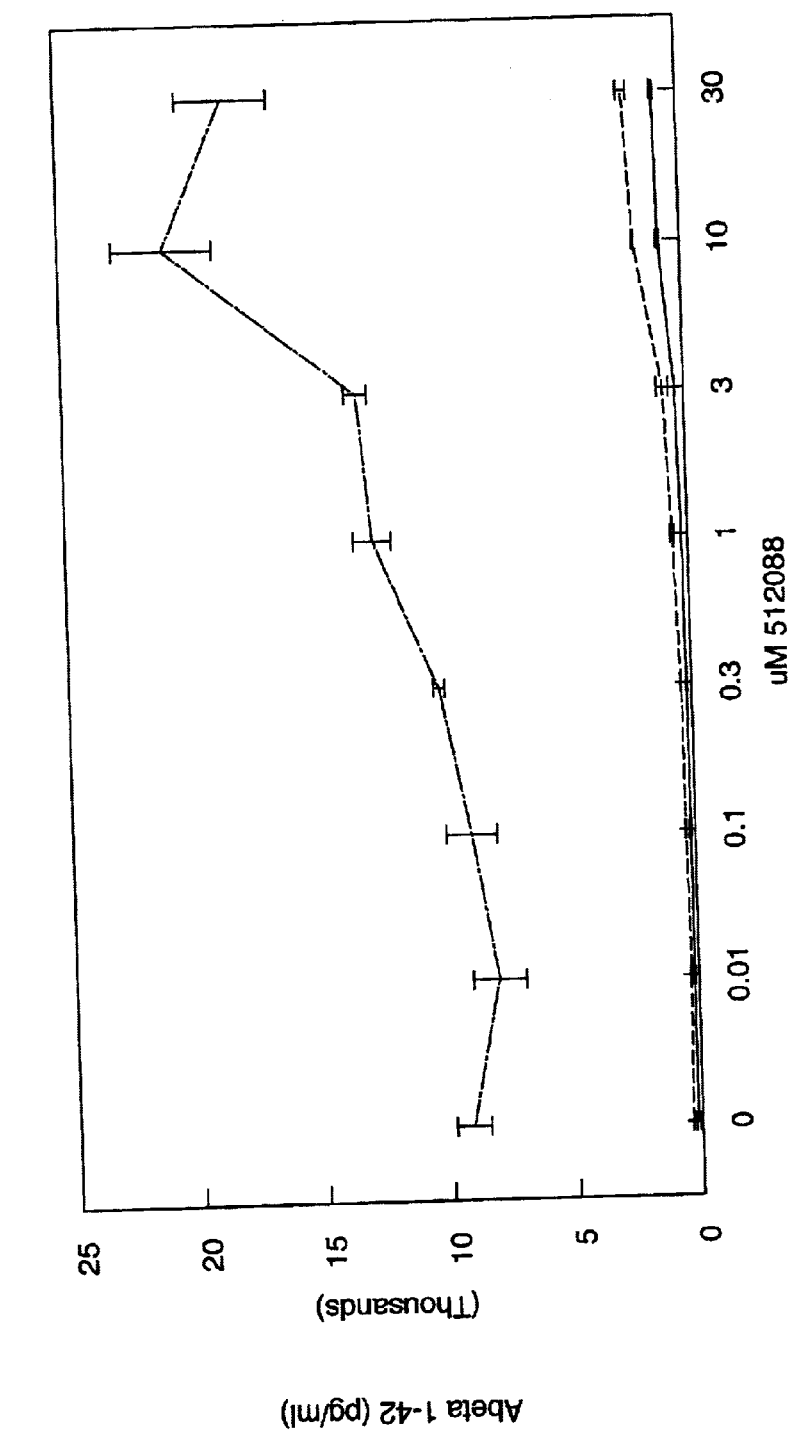

FIG. 3 shows that the dose response profile of 512088 on the two PS1wt cell lines was distinctly biphasic in inhibition of $A\beta_{1-40}$. This profile was not so apparent in the DTG385 cell line but inhibition was achieved at concentrations of 512088 beginning at 1–2 uM versus 10 uM for the PS1wt cell lines. The biphasic dose response was in this case muted in comparison to the $A\beta_{1-42}$ dose response in the PS1DTG385 cell line (FIG. 4). However the dose response for the levels of $A\beta_{1-42}$ secreted from the PS1-TG385 cell line is clearly biphasic (FIG. 4) and resembles the dose response for $A\beta_{1-40}$ from the PS1wt cell lines. The levels of $A\beta_{1-42}$ are increased significantly with respect to A$\beta$40 when the cell line co-expresses PS1-DTG385 (FIG. 4). The inhibitory phase of the dose response for $A\beta_{1-42}$ occurs at ~10 uM 512088 in the PS1-DTG385 cells whereas for the PS1wt cells the inhibitory phase has not started at 30 uM . Above this concentration of drug cellular toxicity becomes an issue.

Figure 5:
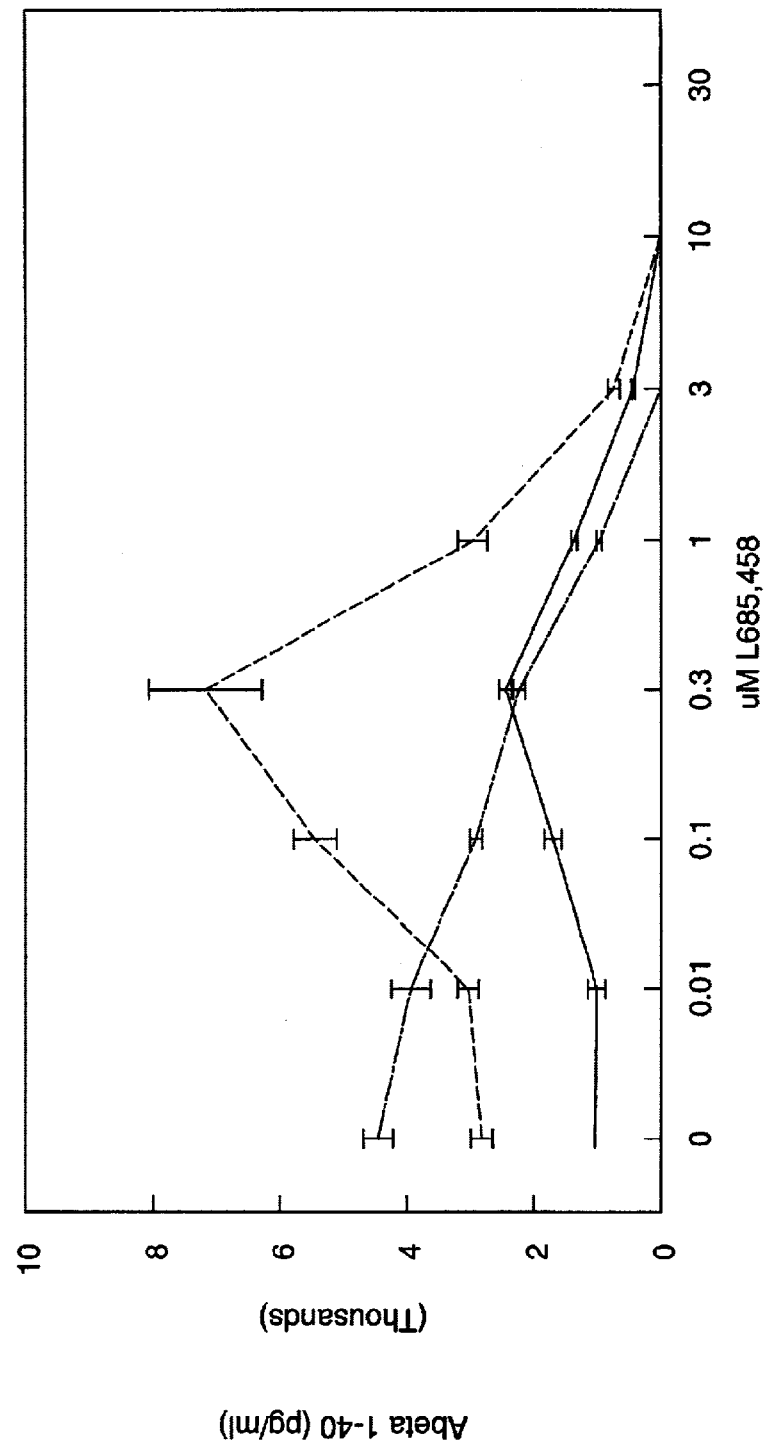
Figure 6:
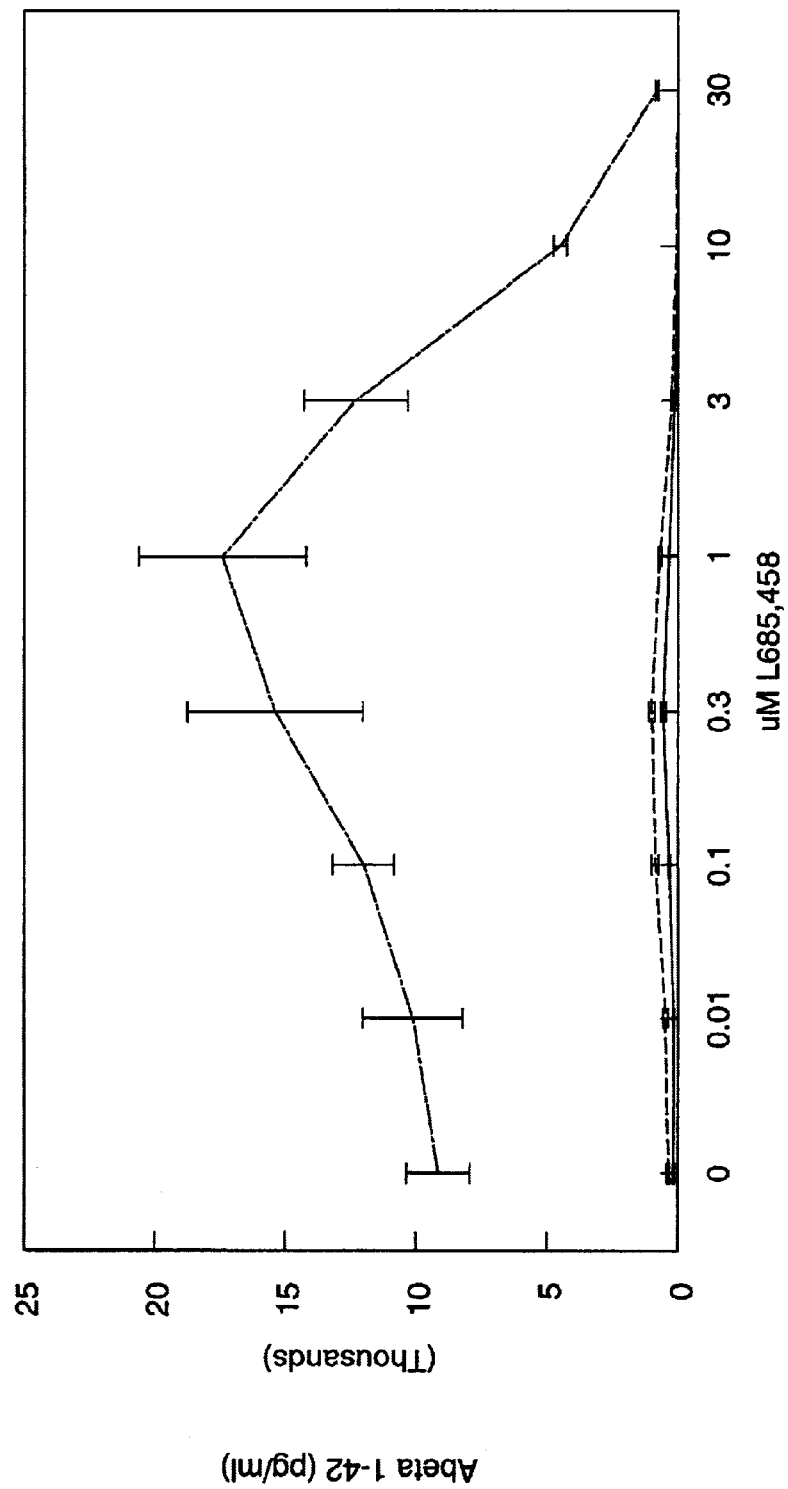

FIG. 5 shows the treatment of the cells with L685,458. The PS1-DTG385 cell line responded to drug with a linear decrease in $A\beta_{1-40}$ production as drug concentration increased. Both of the PS1wt cell lines gave a biphasic dose response. However all three cell lines gave a biphasic dose reponse with respect to $A\beta_{1-42}$ production (FIG. 6). The potency of L685,458 is approximately 10 fold greater that 512088.

Figure 7:
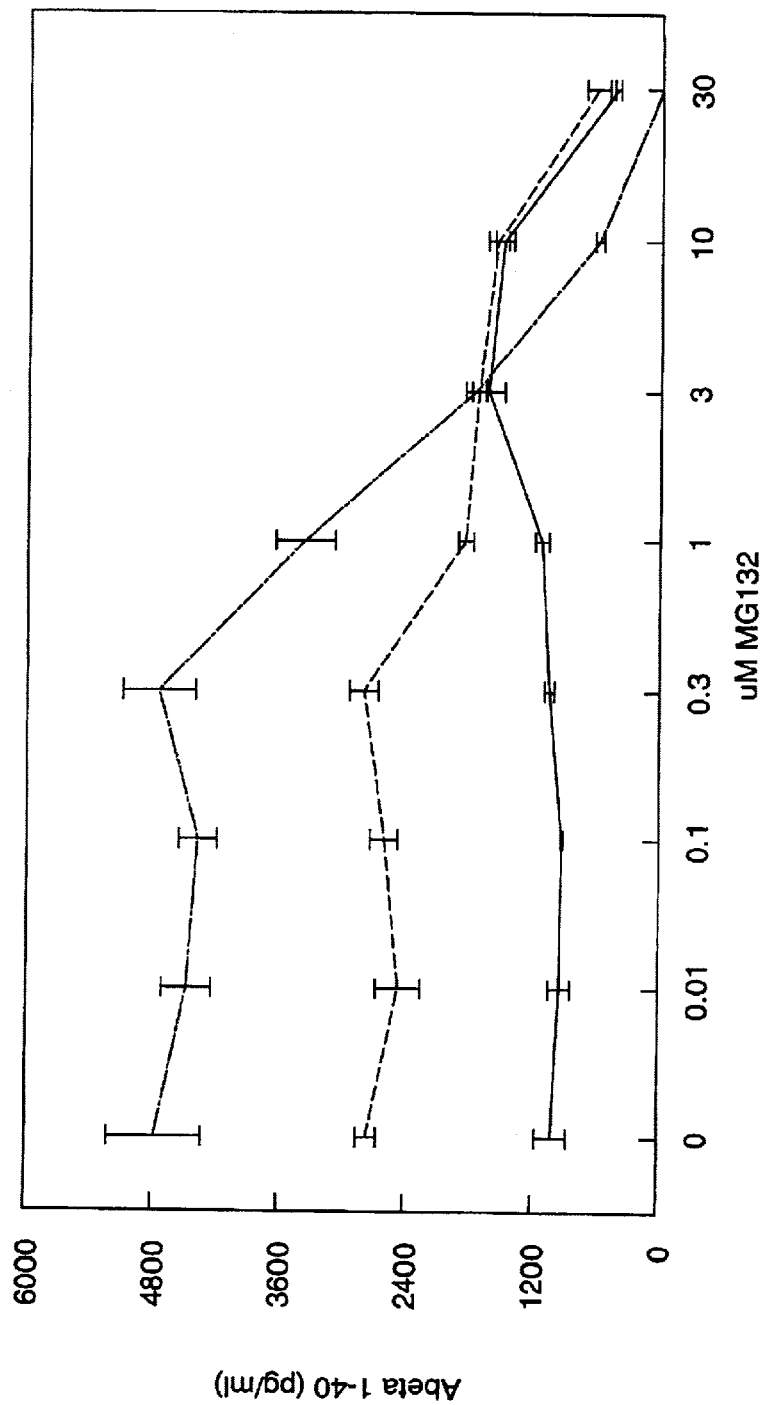
Figure 8:
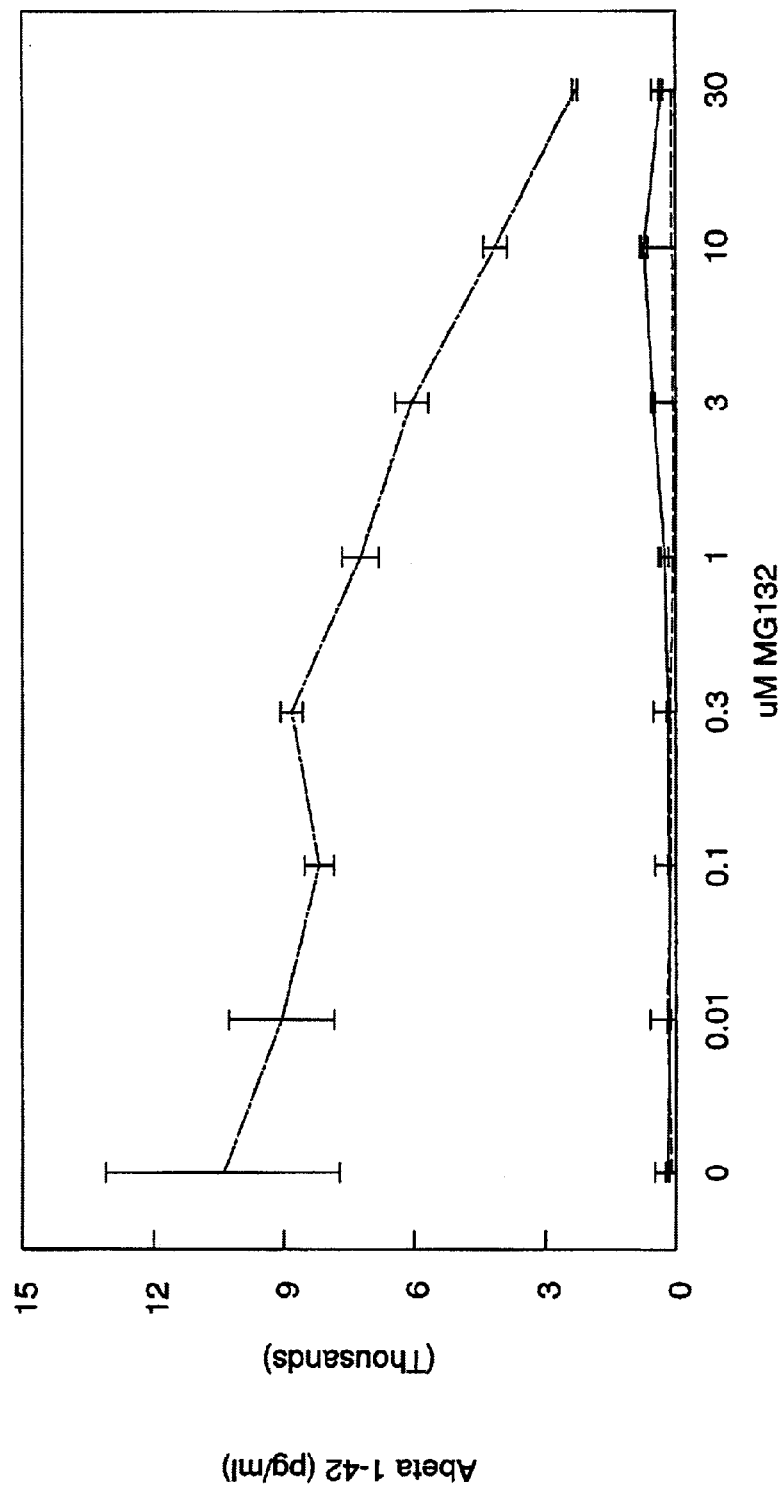

FIGS. 7 and 8 show the effects of the proteosome inhibitor MG132 on $A\beta_{1-40}$ and $A\beta_{1-42}$ production respectively. Inhibition of $A\beta_{1-42}$ $A\beta_{1-40}$ production by MG132 is not strongly biphasic in any of the cell lines except the parental PS1wt HEK125.3-16 (FIG. 7). Inhibition of A$\beta$ $A\beta_{1-42}$ is not strongly biphasic in the PS1-DTG385 cells but the slight increase in A$\beta$ $A\beta_{1-42}$ detected in the media at doses from 0.1 to 0.3 uM suggest that this inhibition curve is biphasic (FIG. 8). The inhibition curve for the two PS1wt cell lines is strongly biphasic. The peaks in the dose response for the PS1wt occurs at 10 uM whereas for the PS1DTG385 the peak is lower (0.3 uM).

Figure 9:
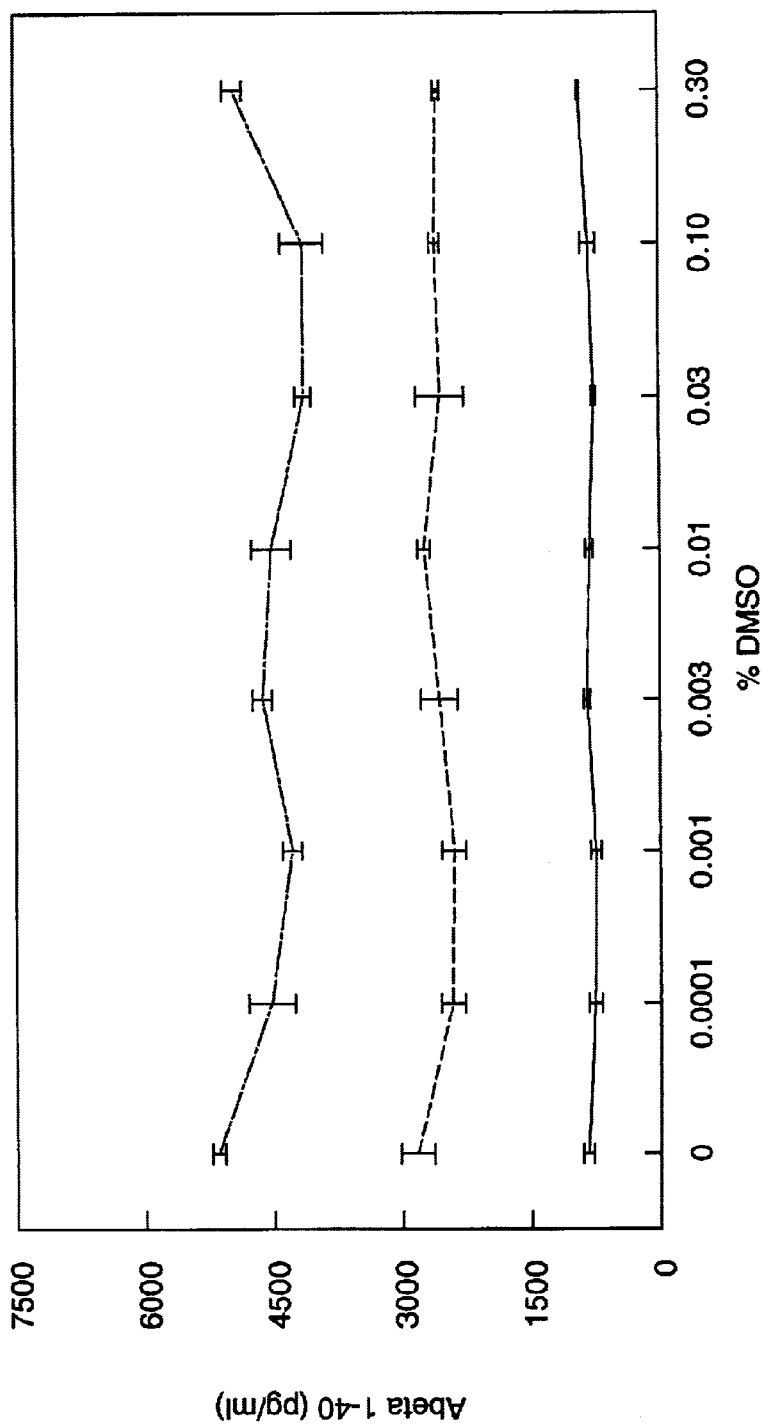
Figure 10:
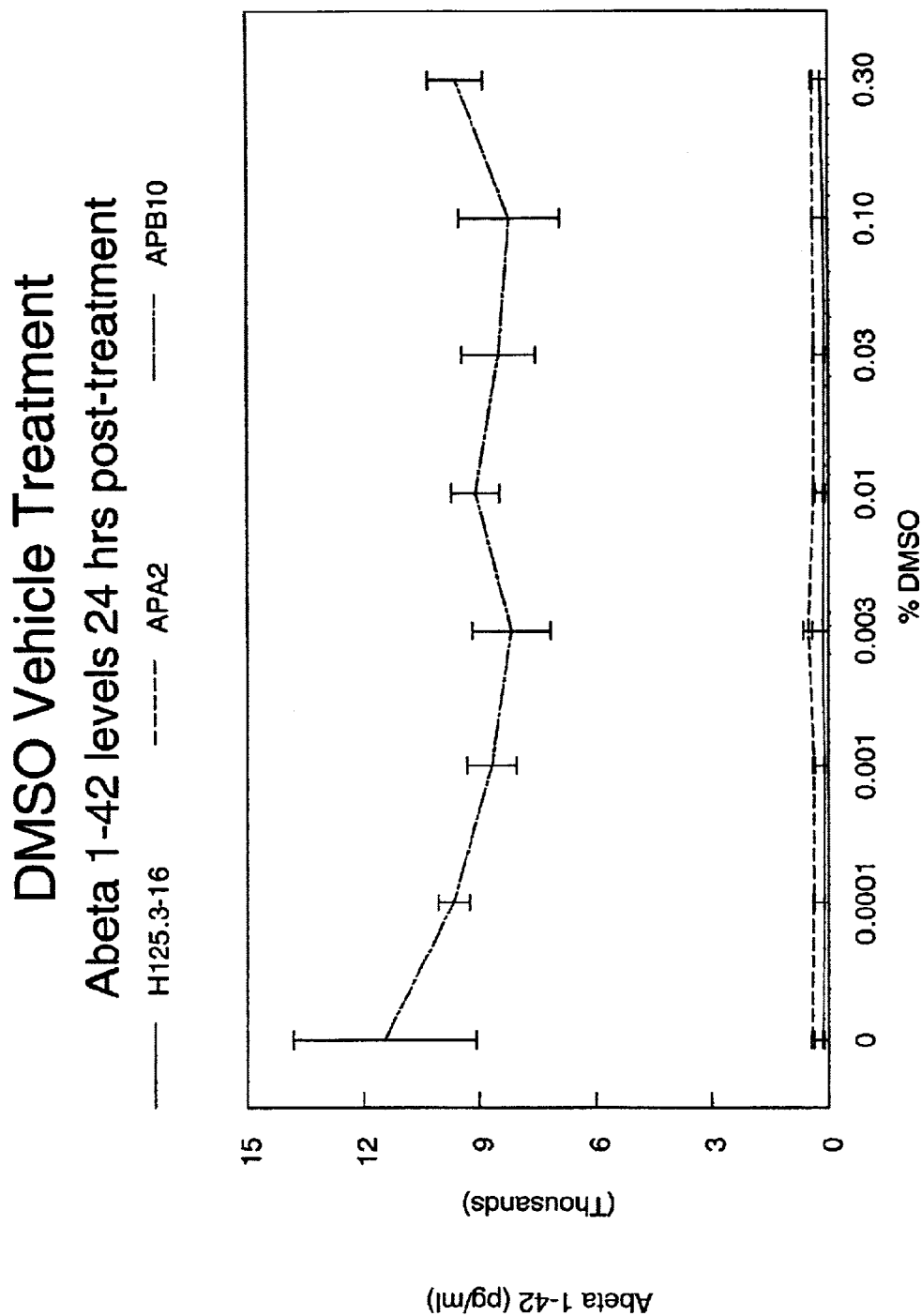

FIGS. 9 and 10 demonstrate that the DMSO vehicle has no effect on the ability of the cells to produce $A\beta_{1-40}$ or $A\beta_{1-42}$.

Discussion

It has already been demonstrated in the previous example that the PS1DTG385 mutations selectively and robustly increase the secretion of $A\beta_{1-42}$ relative to $A\beta_{1-40}$ in HEK cells expressing APPsw constructs. The inhibition dose response of the L685,458 compound with respect to $A\beta_{1-40}$ displays a different profile dependent on whether the PS1wt or PS1DTG385 constructs have been transfected into the cells. However the dose response for L685,458 on the PS1DTG385 cells is clearly biphasic and except for being shifted to slightly lower potency, similar to that of the PS1wt cell lines. This implies that the activity comprised by the PS1DTG385 construct is similar to that of the PS1wt activity in the production of $A\beta_{1-42}$. The activity of the PS1DTG385 construct seems to confer a different response to the protease inhibitors used in this study from the PS1wt activity in production of $A\beta_{1-40}$. Response to the proteasome inhibitor MG132 appears to be similar for all three cell lines with respect to secretion of $A\beta_{1-40}$ but differs significantly with respect to $A\beta_{1-42}$. As observed by Marambaud et al. (P. Marambaud et al Molecular Medicine v. 4:147–157, 1998.) MG132 appears to potentiate the production of $A\beta_{1-42}$ relative to $A\beta_{1-40}$ at doses ranging from 0.3 uM to 10 uM in PS1wt cells. This does not happen when MG132 is applied to the PS1DTG385 cells in this study. Thus the activity expressed by the PS1DTG385 construct appears to modify the dose response of both A$\beta$40 and 42 to known gamma-secretase inhibitors. In the case of the most specific compound for gamma-secretase inhibition, L685,458, the activity of the PS1DTG385 construct looks very similar to that of the PS1wt c Transgenic Animals of the Invention The present invention provides a tool for analyzing the molecular mechanism of presenilin action and the pathogenesis of Alzheimer's Disease. More specifically, it elucidates the mechanism underlying APP processing after synthesis of these proteins. More importantly, it provides an in vivo screening system for drugs that can inhibit synthesis and deposition of beta amyloid $A\beta_{1-42}$, and thereby prevent or alleviate the symptoms of Alzheimer's Disease.

A DNA fragment encoding a mutant presenilin may be integrated into the genome of the transgenic animal by any standard method such as are described in Hogan et al., MANIPULATING THE MOUSE EMBRYO, Cold Spring Harbor Laboratory Press, 1986; Kraemer et al., GENETIC MANIPULATION OF THE EARLY MAMMALIAN EMBRYO, Cold Spring Harbor Laboratory Press, 1985; Krimpenfort et al., U.S. Pat. No. 5,175,384; Krimpenfort at al., Biotechnology, 9: 88 (1991), all of which are incorporated by reference. Preferably, the DNA fragment is microinjected into pronuclei of single-cell embryos in non-human mammalian animals, such as rodents such as mice, rabbits, cats, dogs or larger domestic or farm animals.

These injected embryos are transplanted to the oviducts/uteri of pseudopregnant females and finally transgenic animals can be obtained. These transgenic animals are overexpress or express at physiologic levels the mutant PS1 and PS2 of the invention. The injected DNA contains an ubiquitous promoter to drive expression of the mutant PS1 or PS2 polypeptides in various types of the cells in transgenic mice. Preferably the transgenic mice of the invention also overexpress APP, more preferably the APP is altered to contain either the Swedish mutation. (McConlogue U.S. Pat. Nos. 5,850,003 and 5,612,486 herein incorporated by reference.) or the London mutation In some embodiments, it is preferable that the transgene sequences encoding the mutant PS1 and PS2 polypeptides are under the transcriptional control of promoters and/or enhancers (and/or silencers) which are "neuron specific promoters'. Such promoters confer high level expression and/or in a cell type-specific expression pattern in neuronal cell types. The rat neural-specific enolase (NSE) promoter (Forss-Petter (1990) Neuron 5; 137) is a preferred transcriptional regulatory element for operable linkage to a nucleotide sequence encoding a mutant PS1 or PS2 polypeptide. Other promoters and/or enhancers which confer efficient expression to the transgene-encoded mutant PS1 or PS2 sequence in brain tissue generally are preferred.

Various promoters having different strengths (e.g., pgk, tk, dhfr) may be substituted in the discretion of the practitioner, however it is essential that the promoter function in the nonhuman host and it is desirable in some embodiments that the promoter drive expression in a developmental pattern or cell type-specific pattern (and at expression levels) similar to a naturally-occurring PS1 or PS2 gene in a parallel host animal lacking the transgene. As a result, the following phenotypic alteration can be elicited:

AD-specific amyloid deposition at hippocampus, appearance of abnormally phosphorylated tau protein, increase in the number of glial cells, alteration in the alternative splicing pattern of endogenous mouse APP transcripts, neuronal cell death near hippocampus and reduced behavioral activity. Accordingly, the transgenic animal disclosed in the present invention provides a useful system to analyze the interaction between APP and the mutant PS1 and PS2-processing protease in vivo, and the interaction between the endogenous mouse APP and the optionally introduced human APP. They are also useful for screening anti-AD drugs in vivo.

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention. It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

SEQUENCE LISTING

```
<160> NUMBER OF SEQ ID NOS: 20

<210> SEQ ID NO 1
<211> LENGTH: 1404
<212> TYPE: DNA
<213> ORGANISM: Homo sapiens
<220> FEATURE:
<221> NAME/KEY: variation
<222> LOCATION: (772)..(777)
<223> OTHER INFORMATION: site directed mutagensis sites

<400> SEQUENCE: 1
atgacagagt tacctgcacc gttgtcctac ttccagaatg cacagatgtc tgaggacaac     60
cacctgagca atactgtacg tagccagaat gacaatagag aacggcagga gcacaacgac    120
agacggagcc ttggccaccc tgagccatta tctaatggac gaccccaggg taactcccgg    180
caggtggtgg agcaagatga ggaagaagat gaggagctga cattgaaata tggcgccaag    240
catgtgatca tgctctttgt ccctgtgact ctctgcatgt tggtggtcgt ggctaccatt    300
aagtcagtca gcttttatac ccggaaggat gggcagctaa tctataccccc attcacagaa    360 gataccgaga ctgtgggcca gagagccctg cactcaattc tgaatgctgc catcatgatc    420
agtgtcattg ttgtcatgac tatcctcctg gtggttctgt ataaatacag gtgctataag    480
gtcatccatg cctggcttat tatatcatct ctattgttgc tgttctttttt ttcattcatt    540 tacttggggg aagtgtttaa aacctataac gttgctgtgg actacattac tgttgcactc    600
ctgatctgga attttggtgt ggtgggaatg atttccattc actggaaagg tccacttcga    660
ctccagcagg catatctcat tatgattagt gccctcatgg ccctggtgtt tatcaagtac    720
ctccctgaat ggactgcgtg gctcatcttg gctgtgattt cagtatatga tnnnnnngct    780
gttttgtgtc cgaaaggtcc acttcgtatg ctggttgaaa cagctcagga gagaaatgaa    840 acgcttttttc cagctctcat ttactcctca acaatggtgt ggttggtgaa tatggcagaa    900
ggagacccgg aagctcaaag gagagtatcc aaaaattcca agtataatgc agaaagcaca    960
gaaagggagt cacaagacac tgttgcagag aatgatgatg gcgggttcag tgaggaatgg   1020
gaagcccaga gggacagtca tctagggcct catcgctcta cacctgagtc acgagctgct   1080
gtccaggaac tttccagcag tatcctcgct ggtgaagacc cagaggaaag gggagtaaaa   1140
cttggattgg gagatttcat tttctacagt gttctggttg gtaaagcctc agcaacagcc   1200
agtggagact ggaacacaac catagcctgt ttcgtagcca tattaattgg tttgtgcctt   1260
```

```
acattattac tccttgccat tttcaagaaa gcattgccag ctcttccaat ctccatcacc    1320
tttgggcttg ttttctactt tgccacagat tatcttgtac agccttttat ggaccaatta    1380
gcattccatc aattttatat ctag                                          1404

<210> SEQ ID NO 2
<211> LENGTH: 1404
<212> TYPE: DNA
<213> ORGANISM: Homo sapiens
<220> FEATURE:
<221> NAME/KEY: variation
<222> LOCATION: (1156)..(1161)
<223> OTHER INFORMATION: site directed mutagenesis sites

<400> SEQUENCE: 2
atgacagagt tacctgcacc gttgtcctac ttccagaatg cacagatgtc tgaggacaac      60
cacctgagca atactgtacg tagccagaat gacaatagag aacggcagga gcacaacgac     120
agacggagcc ttggccaccc tgagccatta tctaatggac daccccaggg taactcccgg     180
caggtggtgg agcaagatga ggaagaagat gaggagctga cattgaaata tggcgccaag     240
catgtgatca tgctctttgt ccctgtgact ctctgcatgg tggtggtcgt ggctaccatt     300
aagtcagtca gcttttatac ccggaaggat gggcagctaa tctataccccc attcacagaa     360 gataccgaga ctgtgggcca gagagccctg cactcaattc tgaatgctgc catcatgatc     420
agtgtcattg ttgtcatgac tatcctcctg gtggttctgt ataaatacag gtgctataag     480
gtcatccatg cctggcttat tatatcatct ctattgttgc tgttcttttt ttcattcatt     540
tacttggggg aagtgtttaa aacctataac gttgctgtgg actacattac tgttgcactc     600
ctgatctgga attttggtgt ggtgggaatg atttccattc actggaaagg tccacttcga     660
ctccagcagg catatctcat tatgattagt gccctcatgg ccctggtgtt tatcaagtac     720
ctccctgaat ggactgcgtg gctcatcttg gctgtgattt cagtatatga tttagtggct     780
gttttgtgtc cgaaaggtcc acttcgtatg ctggttgaaa cagctcagga gagaaatgaa     840 acgcttttc cagctctcat ttactcctca acaatggtgt ggttggtgaa tatggcagaa     900
ggagacccgg aagctcaaag gagagtatcc aaaaattcca agtataatgc agaaagcaca     960
gaaagggagt cacaagacac tgttgcagag aatgatgatg gcgggttcag tgaggaatgg    1020
gaagcccaga gggacagtca tctagggcct catcgctcta cacctgagtc acgagctgct    1080
gtccaggaac tttccagcag tatcctcgct ggtgaagacc cagaggaaag gggagtaaaa    1140
cttggattgg gagatnnnnn nttctacagt gttctggttg gtaaagcctc agcaacagcc    1200
agtggagact ggaacacaac catagcctgt tcgtagcca tattaattgg tttgtgcctt    1260
acattattac tccttgccat tttcaagaaa gcattgccag ctcttccaat ctccatcacc    1320
tttgggcttg ttttctactt tgccacagat tatcttgtac agccttttat ggaccaatta    1380
gcattccatc aattttatat ctag                                          1404

<210> SEQ ID NO 3
<211> LENGTH: 1404
<212> TYPE: DNA
<213> ORGANISM: Homo sapiens
<220> FEATURE:
<221> NAME/KEY: variation
<222> LOCATION: (772)..(777)
<223> OTHER INFORMATION: site directed mutagenesis sites
<220> FEATURE:
<221> NAME/KEY: variation
<222> LOCATION: (1156)..(1161)
<223> OTHER INFORMATION: site directed mutagenesis site
```

<400> SEQUENCE: 3

```
atgacagagt tacctgcacc gttgtcctac ttccagaatg cacagatgtc tgaggacaac      60
cacctgagca atactgtacg tagccagaat gacaatagag aacggcagga gcacaacgac     120
agacggagcc ttggccaccc tgagccatta tctaatggac gacccaggg taactcccgg      180
caggtggtgg agcaagatga ggaagaagat gaggagctga cattgaaata tggcgccaag     240
catgtgatca tgctctttgt ccctgtgact ctctgcatgg tggtggtcgt ggctaccatt     300
aagtcagtca gcttttatac ccggaaggat gggcagctaa tctataccc attcacagaa      360
gataccgaga ctgtgggcca gagagccctg cactcaattc tgaatgctgc catcatgatc     420
agtgtcattg ttgtcatgac tatcctcctg gtggttctgt ataaatacag gtgctataag     480
gtcatccatg cctggcttat tatatcatct ctattgttgc tgttcttttt ttcattcatt     540
tacttggggg aagtgtttaa aacctataac gttgctgtgg actacattac tgttgcactc     600
ctgatctgga attttggtgt ggtgggaatg atttccattc actggaaagg tccacttcga     660
ctccagcagg catatctcat tatgattagt gccctcatgg ccctggtgtt tatcaagtac     720
ctccctgaat ggactgcgtg gctcatcttg gctgtgattt cagtatatga tnnnnnngct     780
gttttgtgtc cgaaaggtcc acttcgtatg ctggttgaaa cagctcagga gagaaatgaa     840
acgcttttc cagctctcat ttactcctca acaatggtgt ggttggtgaa tatggcagaa      900
ggagacccgg aagctcaaag gagagtatcc aaaaattcca agtataatgc agaaagcaca     960
gaaagggagt cacaagacac tgttgcagag aatgatgatg gcgggttcag tgaggaatgg    1020
gaagcccaga gggacagtca tctagggcct catcgctcta cacctgagtc acgagctgct    1080
gtccaggaac tttccagcag tatcctcgct ggtgaagacc cagaggaaag ggagtaaaa     1140
cttggattgg gagatnnnnn nttctacagt gttctggttg gtaaagcctc agcaacagcc    1200
agtggagact ggaacacaac catagcctgt ttcgtagcca tattaattgg tttgtgcctt    1260
acattattac tccttgccat tttcaagaaa gcattgccag ctcttccaat ctccatcacc    1320
tttgggcttg ttttctactt tgccacagat tatcttgtac agcctttat ggaccaatta     1380
gcattccatc aattttatat ctag                                           1404
```

<210> SEQ ID NO 4
<211> LENGTH: 467
<212> TYPE: PRT
<213> ORGANISM: Homo sapiens
<220> FEATURE:
<221> NAME/KEY: VARIANT
<222> LOCATION: (258)..(259)
<223> OTHER INFORMATION: site directed mutagenesis site

<400> SEQUENCE: 4

```
Met Thr Glu Leu Pro Ala Pro Leu Ser Tyr Phe Gln Asn Ala Gln Met
 1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
```

```
                        85                  90                  95
Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Xaa Xaa Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
370                 375                 380

Asp Phe Ile Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 5
<211> LENGTH: 467
<212> TYPE: PRT
<213> ORGANISM: Homo sapiens
```

```
<220> FEATURE:
<221> NAME/KEY: VARIANT
<222> LOCATION: (386)..(387)
<223> OTHER INFORMATION: site directed mutagensis site

<400> SEQUENCE: 5
```

| | | | | | | | | | | | | | | | |
|---|---|---|---|---|---|---|---|---|---|---|---|---|---|---|---|
| Met | Thr | Glu | Leu | Pro | Ala | Pro | Leu | Ser | Tyr | Phe | Gln | Asn | Ala | Gln | Met |
| 1 | | | | 5 | | | | | 10 | | | | | 15 | |
| Ser | Glu | Asp | Asn | His | Leu | Ser | Asn | Thr | Val | Arg | Ser | Gln | Asn | Asp | Asn |
| | | | 20 | | | | | 25 | | | | | 30 | | |
| Arg | Glu | Arg | Gln | Glu | His | Asn | Asp | Arg | Arg | Ser | Leu | Gly | His | Pro | Glu |
| | | 35 | | | | | 40 | | | | | 45 | | | |
| Pro | Leu | Ser | Asn | Gly | Arg | Pro | Gln | Gly | Asn | Ser | Arg | Gln | Val | Val | Glu |
| | 50 | | | | | 55 | | | | | 60 | | | | |
| Gln | Asp | Glu | Glu | Glu | Asp | Glu | Leu | Thr | Leu | Lys | Tyr | Gly | Ala | Lys |
| 65 | | | | | 70 | | | | 75 | | | | | 80 |
| His | Val | Ile | Met | Leu | Phe | Val | Pro | Val | Thr | Leu | Cys | Met | Val | Val | Val |
| | | | | 85 | | | | | 90 | | | | | 95 | |
| Val | Ala | Thr | Ile | Lys | Ser | Val | Ser | Phe | Tyr | Thr | Arg | Lys | Asp | Gly | Gln |
| | | | 100 | | | | | 105 | | | | | 110 | | |
| Leu | Ile | Tyr | Thr | Pro | Phe | Thr | Glu | Asp | Thr | Glu | Thr | Val | Gly | Gln | Arg |
| | | 115 | | | | | 120 | | | | | 125 | | | |
| Ala | Leu | His | Ser | Ile | Leu | Asn | Ala | Ala | Ile | Met | Ile | Ser | Val | Ile | Val |
| | 130 | | | | | 135 | | | | | 140 | | | | |
| Val | Met | Thr | Ile | Leu | Leu | Val | Val | Leu | Tyr | Lys | Tyr | Arg | Cys | Tyr | Lys |
| 145 | | | | | 150 | | | | | 155 | | | | | 160 |
| Val | Ile | His | Ala | Trp | Leu | Ile | Ile | Ser | Ser | Leu | Leu | Leu | Leu | Phe | Phe |
| | | | | 165 | | | | | 170 | | | | | 175 | |
| Phe | Ser | Phe | Ile | Tyr | Leu | Gly | Glu | Val | Phe | Lys | Thr | Tyr | Asn | Val | Ala |
| | | | 180 | | | | | 185 | | | | | 190 | | |
| Val | Asp | Tyr | Ile | Thr | Val | Ala | Leu | Leu | Ile | Trp | Asn | Phe | Gly | Val | Val |
| | | 195 | | | | | 200 | | | | | 205 | | | |
| Gly | Met | Ile | Ser | Ile | His | Trp | Lys | Gly | Pro | Leu | Arg | Leu | Gln | Gln | Ala |
| | 210 | | | | | 215 | | | | | 220 | | | | |
| Tyr | Leu | Ile | Met | Ile | Ser | Ala | Leu | Met | Ala | Leu | Val | Phe | Ile | Lys | Tyr |
| 225 | | | | | 230 | | | | | 235 | | | | | 240 |
| Leu | Pro | Glu | Trp | Thr | Ala | Trp | Leu | Ile | Leu | Ala | Val | Ile | Ser | Val | Tyr |
| | | | | 245 | | | | | 250 | | | | | 255 | |
| Asp | Leu | Val | Ala | Val | Leu | Cys | Pro | Lys | Gly | Pro | Leu | Arg | Met | Leu | Val |
| | | | 260 | | | | | 265 | | | | | 270 | | |
| Glu | Thr | Ala | Gln | Glu | Arg | Asn | Glu | Thr | Leu | Phe | Pro | Ala | Leu | Ile | Tyr |
| | | 275 | | | | | 280 | | | | | 285 | | | |
| Ser | Ser | Thr | Met | Val | Trp | Leu | Val | Asn | Met | Ala | Glu | Gly | Asp | Pro | Glu |
| | 290 | | | | | 295 | | | | | 300 | | | | |
| Ala | Gln | Arg | Arg | Val | Ser | Lys | Asn | Ser | Lys | Tyr | Asn | Ala | Glu | Ser | Thr |
| 305 | | | | | 310 | | | | | 315 | | | | | 320 |
| Glu | Arg | Glu | Ser | Gln | Asp | Thr | Val | Ala | Glu | Asn | Asp | Asp | Gly | Gly | Phe |
| | | | | 325 | | | | | 330 | | | | | 335 | |
| Ser | Glu | Glu | Trp | Glu | Ala | Gln | Arg | Asp | Ser | His | Leu | Gly | Pro | His | Arg |
| | | | 340 | | | | | 345 | | | | | 350 | | |
| Ser | Thr | Pro | Glu | Ser | Arg | Ala | Ala | Val | Gln | Glu | Leu | Ser | Ser | Ser | Ile |
| | | 355 | | | | | 360 | | | | | 365 | | | |
| Leu | Ala | Gly | Glu | Asp | Pro | Glu | Glu | Arg | Gly | Val | Lys | Leu | Gly | Leu | Gly |
| | 370 | | | | | 375 | | | | | 380 | | | | |

-continued

```
Asp Xaa Xaa Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
                420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 6
<211> LENGTH: 467
<212> TYPE: PRT
<213> ORGANISM: Homo sapiens
<220> FEATURE:
<221> NAME/KEY: VARIANT
<222> LOCATION: (258)..(259)
<223> OTHER INFORMATION: site directed mutagenesis site
<220> FEATURE:
<221> NAME/KEY: VARIANT
<222> LOCATION: (386)..(387)
<223> OTHER INFORMATION: site directed mutagenesis site

<400> SEQUENCE: 6

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
                20                  25                  30

Arg Glu Arg Gln Glu His Asn Asp Arg Arg Ser Leu Gly His Pro Glu
            35                  40                  45

Pro Leu Ser Asn Gly Arg Pro Gln Gly Asn Ser Arg Gln Val Val Glu
        50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175

Phe Ser Phe Ile Tyr Leu Gly Glu Val Phe Lys Thr Tyr Asn Val Ala
            180                 185                 190

Val Asp Tyr Ile Thr Val Ala Leu Leu Ile Trp Asn Phe Gly Val Val
        195                 200                 205

Gly Met Ile Ser Ile His Trp Lys Gly Pro Leu Arg Leu Gln Gln Ala
    210                 215                 220

Tyr Leu Ile Met Ile Ser Ala Leu Met Ala Leu Val Phe Ile Lys Tyr
225                 230                 235                 240
```

```
Leu Pro Glu Trp Thr Ala Trp Leu Ile Leu Ala Val Ile Ser Val Tyr
                245                 250                 255

Asp Xaa Xaa Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
    290                 295                 300

Ala Gln Arg Arg Val Ser Lys Asn Ser Lys Tyr Asn Ala Glu Ser Thr
305                 310                 315                 320

Glu Arg Glu Ser Gln Asp Thr Val Ala Glu Asn Asp Asp Gly Gly Phe
                325                 330                 335

Ser Glu Glu Trp Glu Ala Gln Arg Asp Ser His Leu Gly Pro His Arg
            340                 345                 350

Ser Thr Pro Glu Ser Arg Ala Ala Val Gln Glu Leu Ser Ser Ser Ile
        355                 360                 365

Leu Ala Gly Glu Asp Pro Glu Glu Arg Gly Val Lys Leu Gly Leu Gly
    370                 375                 380

Asp Xaa Xaa Phe Tyr Ser Val Leu Val Gly Lys Ala Ser Ala Thr Ala
385                 390                 395                 400

Ser Gly Asp Trp Asn Thr Thr Ile Ala Cys Phe Val Ala Ile Leu Ile
                405                 410                 415

Gly Leu Cys Leu Thr Leu Leu Leu Ala Ile Phe Lys Lys Ala Leu
            420                 425                 430

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 7
<211> LENGTH: 1347
<212> TYPE: DNA
<213> ORGANISM: Homo sapiens
<220> FEATURE:
<221> NAME/KEY: variation
<222> LOCATION: (790)..(795)
<223> OTHER INFORMATION: site directed mutagenesis site

<400> SEQUENCE: 7
atgctcacat tcatggcctc tgacagcgag gaagaagtgt gtgatgagcg gacgtccctg      60
atgtcggccg agagccccac gccgcgctcc tgccaggagg caggcagggg cccagaggat     120
ggagagaaca ctgcccagtg gagaagccag gagaacgagg aggacggtga ggaggaccct     180
gaccgctatg tctgtagtgg ggttcccggg cggccgccag gctggaggag agctgacc      240 ctcaaatacg gagcgaagca cgtgatcatg ctgtttgtgc ctgtcactct gtgcatgatc     300
gtggtggtag ccaccatcaa gtctgtgcgc ttctacacag agaagaatgg acagctcatc     360
tacacgacat tcactgagga cacaccctcg gtgggccagc gcctcctcaa ctccgtgctg     420
aacaccctca tcatgatcag cgtcatcgtg gttatgacca tcttcttggt ggtgctctac     480
aagtaccgct gctacaagtt catccatggc tggttgatca tgtcttcact gatgctgctg     540
ttcctcttca cctatatcta ccttggggaa gtgctcaaga cctacaatgt ggccatggac     600
taccccaccc tcttgctgac tgtctggaac ttcggggcag tgggcatggt gtgcatccac     660
```

-continued

| | |
|---|---|
| tggaagggcc ctctggtgct gcagcaggcc tacctcatca tgatcagtgc gctcatggcc | 720 |
| ctagtgttca tcaagtacct cccagagtgg tccgcgtggg tcatcctggg cgccatctct | 780 |
| gtgtatgatn nnnnngctgt gctgtgtccc aaagggcctc tgagaatgct ggtagaaact | 840 |
| gcccaggaga gaaatgagcc catattccct gccctgatat actcatctgc catggtgtgg | 900 |
| acggttggca tggcgaagct ggacccctcc tctcagggtg ccctccagct cccctacgac | 960 |
| ccggagatgg aagaagactc ctatgacagt tttggggagc cttcataccc cgaagtcttt | 1020 |
| gagcctccct tgactggcta cccaggggag gagctggagg aagaggagga aaggggcgtg | 1080 |
| aagcttggcc tcggggactt catcttctac agtgtgctgg tgggcaaggc ggctgccacg | 1140 |
| ggcagcgggg actggaatac cacgctggcc tgcttcgtgg ccatcctcat tggcttgtgt | 1200 |
| ctgaccctcc tgctgcttgc tgtgttcaag aaggcgctgc ccgccctccc catctccatc | 1260 |
| acgttcgggc tcatcttta cttctccacg gacaacctgg tgcggccgtt catggacacc | 1320 |
| ctggcctccc atcagctcta catctga | 1347 |

<210> SEQ ID NO 8
<211> LENGTH: 1347
<212> TYPE: DNA
<213> ORGANISM: Homo sapiens
<220> FEATURE:
<221> NAME/KEY: variation
<222> LOCATION: (1099)..(1104)
<223> OTHER INFORMATION: site directed mutagenesis site

<400> SEQUENCE: 8

| | |
|---|---|
| atgctcacat tcatggcctc tgacagcgag gaagaagtgt gtgatgagcg gacgtcccta | 60 |
| atgtcggccg agagccccac gccgcgctcc tgccaggagg gcaggcaggg cccagaggat | 120 |
| ggagagaaca ctgcccagtg gagaagccag gagaacgagg aggacggtga ggaggaccct | 180 |
| gaccgctatg tctgtagtgg ggttcccggg cggccgccag gcctgaggga agagctgacc | 240 |
| ctcaaatacg gagcgaagca cgtgatcatg ctgtttgtgc ctgtcactct gtgcatgatc | 300 |
| gtggtggtag ccaccatcaa gtctgtgcgc ttctacacag agaagaatgg acagctcatc | 360 |
| tacacgacat tcactgagga cacaccctcg gtgggccagc gcctcctcaa ctccgtgctg | 420 |
| aacaccctca tcatgatcag cgtcatcgtg gttatgacca tcttcttggt ggtgctctac | 480 |
| aagtaccgct gctacaagtt catccatggc tggttgatca tgtcttcact gatgctgctg | 540 |
| ttcctcttca cctatatcta ccttggggaa gtgctcaaga cctacaatgt ggccatggac | 600 |
| taccccaccc tcttgctgac tgtctggaac ttcggggcag tgggcatggt gtgcatccac | 660 |
| tggaagggcc tctggtgct gcagcaggcc tacctcatca tgatcagtgc gctcatggcc | 720 |
| ctagtgttca tcaagtacct cccagagtgg tccgcgtggg tcatcctggg cgccatctct | 780 |
| gtgtatgatc tcgtggctgt gctgtgtccc aaagggcctc tgagaatgct ggtagaaact | 840 |
| gcccaggaga gaaatgagcc catattccct gccctgatat actcatctgc catggtgtgg | 900 |
| acggttggca tggcgaagct ggaccctcc tctcagggtg ccctccagct cccctacgac | 960 |
| ccggagatgg aagaagactc ctatgacagt tttggggagc cttcataccc cgaagtcttt | 1020 |
| gagcctccct tgactggcta cccaggggag gagctggagg aagaggagga aaggggcgtg | 1080 |
| aagcttggcc tcggggacnn nnnnttctac agtgtgctgg tgggcaaggc ggctgccacg | 1140 |
| ggcagcgggg actggaatac cacgctggcc tgcttcgtgg ccatcctcat tggcttgtgt | 1200 |
| ctgaccctcc tgctgcttgc tgtgttcaag aaggcgctgc ccgccctccc catctccatc | 1260 |
| acgttcgggc tcatcttta cttctccacg gacaacctgg tgcggccgtt catggacacc | 1320 |

-continued ctggcctccc atcagctcta catctga                                      1347

<210> SEQ ID NO 9
<211> LENGTH: 1347
<212> TYPE: DNA
<213> ORGANISM: Homo sapiens
<220> FEATURE:
<221> NAME/KEY: variation
<222> LOCATION: (790)..(795)
<223> OTHER INFORMATION: site directed mutagenesis site
<220> FEATURE:
<221> NAME/KEY: variation
<222> LOCATION: (1099)..(1104)
<223> OTHER INFORMATION: site directed mutagenesis site

<400> SEQUENCE: 9

```
atgctcacat tcatggcctc tgacagcgag gaagaagtgt gtgatgagcg acgtccccta    60
atgtcggccg agagccccac gccgcgctcc tgccaggagg caggcaggg cccagaggat    120
ggagagaaca ctgcccagtg gagaagccag gagaacgagg aggacggtga ggaggaccct    180
gaccgctatg tctgtagtgg ggttcccggg cggccgccag gctggagga agagctgacc    240
ctcaaatacg gagcgaagca cgtgatcatg ctgtttgtgc ctgtcactct gtgcatgatc    300
gtggtggtag ccaccatcaa gtctgtgcgc ttctacacag agaagaatgg acagctcatc    360
tacacgacat tcactgagga cacccctcg gtgggccagc gcctcctcaa ctccgtgctg    420
aacaccctca tcatgatcag cgtcatcgtg gttatgacca tcttcttggt ggtgctctac    480
aagtaccgct gctacaagtt catccatggc tggttgatca tgtcttcact gatgctgctg    540
ttcctcttca cctatatcta ccttggggaa gtgctcaaga cctacaatgt ggccatggac    600
tacccccaccc tcttgctgac tgtctggaac ttcggggcag tgggcatggt gtgcatccac    660
tggaagggcc ctctggtgct gcagcaggcc tacctcatca tgatcagtgc gctcatggcc    720
ctagtgttca tcaagtacct cccagagtgg tccgcgtggg tcatcctggg cgccatctct    780
gtgtatgatn nnnnngctgt gctgtgtccc aaagggcctc tgagaatgct ggtagaaact    840
gcccaggaga gaaatgagcc catattccct gccctgatat actcatctgc catggtgtgg    900
acggttggca tggcgaagct ggaccccctcc tctcagggtg ccctccagct ccctacgac    960
ccggagatgg aagaagactc ctatgacagt tttgggagc cttcataccc cgaagtcttt    1020
gagcctccct tgactggcta cccaggggag gagctggagg aagaggagga agggcgtg    1080
aagcttggcc tcgggacnn nnnnttctac agtgtgctgg tgggcaaggc ggctgccacg    1140
ggcagcgggg actggaatac cacgctggcc tgcttcgtgg ccatcctcat ggcttgtgt    1200
ctgacccctc tgctgcttgc tgtgttcaag aaggcgctgc ccgccctccc catctccatc    1260
acgttcgggc tcatctttta cttctccacg gacaacctgg tgcggccgtt catggacacc    1320
ctggcctccc atcagctcta catctga                                      1347
```

<210> SEQ ID NO 10
<211> LENGTH: 448
<212> TYPE: PRT
<213> ORGANISM: Homo sapiens
<220> FEATURE:
<221> NAME/KEY: VARIANT
<222> LOCATION: (264)..(265)
<223> OTHER INFORMATION: site directed mutagenesis site

<400> SEQUENCE: 10

Met Leu Thr Phe Met Ala Ser Asp Ser Glu Glu Glu Val Cys Asp Glu
 1               5                  10                  15

```
Arg Thr Ser Leu Met Ser Ala Glu Ser Pro Thr Pro Arg Ser Cys Gln
             20                  25                  30

Glu Gly Arg Gln Gly Pro Glu Asp Gly Glu Asn Thr Ala Gln Trp Arg
         35                  40                  45

Ser Gln Glu Asn Glu Glu Asp Gly Glu Glu Asp Pro Asp Arg Tyr Val
     50                  55                  60

Cys Ser Gly Val Pro Gly Arg Pro Pro Gly Leu Glu Glu Glu Leu Thr
 65              70                  75                      80

Leu Lys Tyr Gly Ala Lys His Val Ile Met Leu Phe Val Pro Val Thr
                 85                  90                  95

Leu Cys Met Ile Val Val Val Ala Thr Ile Lys Ser Val Arg Phe Tyr
             100                 105                 110

Thr Glu Lys Asn Gly Gln Leu Ile Tyr Thr Thr Phe Thr Glu Asp Thr
             115                 120                 125

Pro Ser Val Gly Gln Arg Leu Leu Asn Ser Val Leu Asn Thr Leu Ile
     130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                 165                 170                 175

Leu Met Leu Leu Phe Leu Phe Thr Tyr Ile Tyr Leu Gly Glu Val Leu
             180                 185                 190

Lys Thr Tyr Asn Val Ala Met Asp Tyr Pro Thr Leu Leu Leu Thr Val
             195                 200                 205

Trp Asn Phe Gly Ala Val Gly Met Val Cys Ile His Trp Lys Gly Pro
     210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                 245                 250                 255

Gly Ala Ile Ser Val Tyr Asp Xaa Xaa Ala Val Leu Cys Pro Lys Gly
             260                 265                 270

Pro Leu Arg Met Leu Val Glu Thr Ala Gln Glu Arg Asn Glu Pro Ile
     275                 280                 285

Phe Pro Ala Leu Ile Tyr Ser Ser Ala Met Val Trp Thr Val Gly Met
 290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                 325                 330                 335

Pro Glu Val Phe Glu Pro Pro Leu Thr Gly Tyr Pro Gly Glu Glu Leu
             340                 345                 350

Glu Glu Glu Glu Glu Arg Gly Val Lys Leu Gly Leu Gly Asp Phe Ile
             355                 360                 365

Phe Tyr Ser Val Leu Val Gly Lys Ala Ala Thr Gly Ser Gly Asp
             370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                 405                 410                 415

Pro Ile Ser Ile Thr Phe Gly Leu Ile Phe Tyr Phe Ser Thr Asp Asn
             420                 425                 430
```

```
Leu Val Arg Pro Phe Met Asp Thr Leu Ala Ser His Gln Leu Tyr Ile
            435                 440                 445
```

<210> SEQ ID NO 11
<211> LENGTH: 448
<212> TYPE: PRT
<213> ORGANISM: Homo sapiens
<220> FEATURE:
<221> NAME/KEY: VARIANT
<222> LOCATION: (367)..(368)
<223> OTHER INFORMATION: site directed mutagenesis sites

<400> SEQUENCE: 11

```
Met Leu Thr Phe Met Ala Ser Asp Ser Glu Glu Val Cys Asp Glu
  1               5                  10                  15

Arg Thr Ser Leu Met Ser Ala Glu Ser Pro Thr Pro Arg Ser Cys Gln
                 20                  25                  30

Glu Gly Arg Gln Gly Pro Glu Asp Gly Glu Asn Thr Ala Gln Trp Arg
             35                  40                  45

Ser Gln Glu Asn Glu Glu Asp Gly Glu Asp Pro Asp Arg Tyr Val
         50                  55                  60

Cys Ser Gly Val Pro Gly Arg Pro Pro Gly Leu Glu Glu Leu Thr
 65                  70                  75                  80

Leu Lys Tyr Gly Ala Lys His Val Ile Met Leu Phe Val Pro Val Thr
                 85                  90                  95

Leu Cys Met Ile Val Val Val Ala Thr Ile Lys Ser Val Arg Phe Tyr
                100                 105                 110

Thr Glu Lys Asn Gly Gln Leu Ile Tyr Thr Thr Phe Thr Glu Asp Thr
            115                 120                 125

Pro Ser Val Gly Gln Arg Leu Leu Asn Ser Val Leu Asn Thr Leu Ile
130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
210                 215                 220

Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335
```

```
Pro Glu Val Phe Glu Pro Leu Thr Gly Tyr Pro Gly Glu Leu
            340                 345                 350

Glu Glu Glu Glu Glu Arg Gly Val Lys Leu Gly Leu Gly Asp Xaa Xaa
            355                 360                 365

Phe Tyr Ser Val Leu Val Gly Lys Ala Ala Ala Thr Gly Ser Gly Asp
        370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445

<210> SEQ ID NO 12
<211> LENGTH: 448
<212> TYPE: PRT
<213> ORGANISM: Homo sapiens
<220> FEATURE:
<221> NAME/KEY: VARIANT
<222> LOCATION: (264)..(265)
<223> OTHER INFORMATION: site directed mutagenesis sites
<220> FEATURE:
<221> NAME/KEY: VARIANT
<222> LOCATION: (367)..(368)
<223> OTHER INFORMATION: site directed mutagenesis sites

<400> SEQUENCE: 12

Met Leu Thr Phe Met Ala Ser Asp Ser Glu Glu Glu Val Cys Asp Glu
  1               5                  10                  15

Arg Thr Ser Leu Met Ser Ala Glu Ser Pro Thr Pro Arg Ser Cys Gln
             20                  25                  30

Glu Gly Arg Gln Gly Pro Glu Asp Gly Glu Asn Thr Ala Gln Trp Arg
         35                  40                  45

Ser Gln Glu Asn Glu Glu Asp Gly Glu Glu Asp Pro Asp Arg Tyr Val
     50                  55                  60

Cys Ser Gly Val Pro Gly Arg Pro Pro Gly Leu Glu Glu Glu Leu Thr
 65                  70                  75                  80

Leu Lys Tyr Gly Ala Lys His Val Ile Met Leu Phe Val Pro Val Thr
                 85                  90                  95

Leu Cys Met Ile Val Val Val Ala Thr Ile Lys Ser Val Arg Phe Tyr
            100                 105                 110

Thr Glu Lys Asn Gly Gln Leu Ile Tyr Thr Thr Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220
```

```
Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
            245                 250                 255

Gly Ala Ile Ser Val Tyr Asp Xaa Xaa Ala Val Leu Cys Pro Lys Gly
                260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
                340                 345                 350

Glu Glu Glu Glu Glu Arg Gly Val Lys Leu Gly Leu Gly Asp Xaa Xaa
            355                 360                 365

Phe Tyr Ser Val Leu Val Gly Lys Ala Ala Thr Gly Ser Gly Asp
370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
                420                 425                 430

Leu Val Arg Pro Phe Met Asp Thr Leu Ala Ser His Gln Leu Tyr Ile
        435                 440                 445

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence:PS1
      mutatenesis oligonucleotide

<400> SEQUENCE: 13
gctgtgattt cagtatatga tacaggggct gttttgtgtc cgaaagg            47

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence:PS1
      mutagenesis oligonucleotide

<400> SEQUENCE: 14
cctttcggac acaaaacagc ccctgtatca tatactgaaa tcacagc            47

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence:PS1
      mutagenesis oligonucleotide

<400> SEQUENCE: 15
```

```
gggagtaaaa cttggattgg gagataccgg tttctacagt gttctgg          47

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence:PS1
      mutagenesis oligonucleotide

<400> SEQUENCE: 16
ccagaacact gtagaaaccg gtatctccca atccaagttt tactccc          47

<210> SEQ ID NO 17
<211> LENGTH: 42
<212> TYPE: DNA
<213> ORGANISM: Artificial Sequence
<220> FEATURE:
<223> OTHER INFORMATION: Description of Artificial Sequence:PS2
      mutagenesis oligonucleotides

<400> SEQUENCE: 17
gggcgccatc tctgtgtatg ataccggggc tgtgctgtgt cc               42

<210> SEQ ID NO 18
<211> LENGTH: 42
<212> TYPE: DNA
<213> ORGANISM: Artificial Sequence
<220> FEATURE:
<223> OTHER INFORMATION: Description of Artificial Sequence:PS2
      mutagenesis oligonucleotide

<400> SEQUENCE: 18
ggacacagca cagccccggt atcatacaca gagatggcgc cc               42

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence:PS2
      mutagenesis oligonucleotide

<400> SEQUENCE: 19
gcttggcctc ggggacaccg gcttctacag tgtgctggtg g                41

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence:PS2
      mutagenesis oligonucleotide

<400> SEQUENCE: 20
ccaccagcac actgtagaag ccggtgtccc cgaggccaag c                41
```

What is claimed is:

1. An isolated mutant presenilin-1 polypeptide comprising SEQ ID NO: 5 wherein residue 386 is selected from the group consisting of threonine or conservative substitutions of threonine and wherein residue 387, is selected from the group consisting of glycine or conservative substitutions of glycine and wherein said mutant presenilin-1 polypeptide preferentially modulates the processing of amyloid precursor protein to yield increased levels of $A\beta_{1-42}$ relative to $A\beta_{1-40}$ when compared to a wild type presenilin-1 polypeptide.

2. The isolated mutant presenilin-1 polypeptide of claim 1 wherein residue 386 is selected from the group consisting of threonine and serine.

3. The isolated mutant presenilin-1 polypeptide of claim 1 wherein residue 386 is a threonine and residue 387 is a glycine.

4. The isolated mutant presenilin-1 polypeptide of claim 1 wherein residue 386 is selected from the group consisting of threonine and conservative substitutions of threonine and wherein residue 387 is glycine.

5. The isolated mutant presenilin-1 polypeptide of claim 1 wherein residue 386 is threonine and wherein residue 387 is selected from the group consisting of glycine and conservative substitutions of glycine.

* * * * *

UNITED STATES PATENT AND TRADEMARK OFFICE
CERTIFICATE OF CORRECTION

PATENT NO. : 6,686,449 B2
DATED : February 3, 2004
INVENTOR(S) : Donald Bainbridge Carter et al.

It is certified that error appears in the above-identified patent and that said Letters Patent is hereby corrected as shown below:

Drawings,
Figure 2, delete duplicate line beginning at "151" and ending at "200"

Column 4,
Line 37, replace blank line with -- SEQ ID NO:21 wild type presenilin-1 -- and SEQ ID NO:22 wild type presenilin-2 --
Line 39, replace "Fig. 1 Alignment of wild type and mutant ..." with -- Fig. 1 Alignment of wild type (SEQ ID NO:21) and mutant ... --.
Line 42, replace "Fig. 2 Alignment of wild type and mutant ..." with -- Fig. 2 Alignment of wild type (SEQ ID NO:22) and mutant ... --.
(See Attachment 1)

Sequence Listing,
Please add the attached Sequence Listing SEQ ID NO: 21:

Signed and Sealed this

Ninth Day of November, 2004

JON W. DUDAS
*Director of the United States Patent and Trademark Office*

```
<210>  20
<211>  467
<212>  PRT
<213>  Homo sapiens

<400>  21
```

| | | | | | | | | | | | | | | | |
|---|---|---|---|---|---|---|---|---|---|---|---|---|---|---|---|
| Met | Thr | Glu | Leu | Pro | Ala | Pro | Leu | Ser | Tyr | Phe | Gln | Asn | Ala | Gln | Met |
| 1 | | | | 5 | | | | | 10 | | | | | 15 | |

| | | | | | | | | | | | | | | | |
|---|---|---|---|---|---|---|---|---|---|---|---|---|---|---|---|
| Ser | Glu | Asp | Asn | His | Leu | Ser | Asn | Thr | Val | Arg | Ser | Gln | Asn | Asp | Asn |
| | | | 20 | | | | | 25 | | | | | 30 | | |

| | | | | | | | | | | | | | | | |
|---|---|---|---|---|---|---|---|---|---|---|---|---|---|---|---|
| Arg | Glu | Arg | Gln | Glu | His | Asn | Asp | Arg | Arg | Ser | Leu | Gly | His | Pro | Glu |
| | | | 35 | | | | | 40 | | | | | 45 | | |

| | | | | | | | | | | | | | | | |
|---|---|---|---|---|---|---|---|---|---|---|---|---|---|---|---|
| Pro | Leu | Ser | Asn | Gly | Arg | Pro | Gln | Gly | Asn | Ser | Arg | Gln | Val | Val | Glu |
| | | | 50 | | | | | 55 | | | | | 60 | | |

| | | | | | | | | | | | | | | | |
|---|---|---|---|---|---|---|---|---|---|---|---|---|---|---|---|
| Gln | Asp | Glu | Glu | Glu | Asp | Glu | Glu | Leu | Thr | Leu | Lys | Tyr | Gly | Ala | Lys |
| 65 | | | | | 70 | | | | | 75 | | | | | 80 |

| | | | | | | | | | | | | | | | |
|---|---|---|---|---|---|---|---|---|---|---|---|---|---|---|---|
| His | Val | Ile | Met | Leu | Phe | Val | Pro | Val | Thr | Leu | Cys | Met | Val | Val | Val |
| | | | | 85 | | | | | 90 | | | | | 95 | |

| | | | | | | | | | | | | | | | |
|---|---|---|---|---|---|---|---|---|---|---|---|---|---|---|---|
| Val | Ala | Thr | Ile | Lys | Ser | Val | Ser | Phe | Tyr | Thr | Arg | Lys | Asp | Gly | Gln |
| | | | | 100 | | | | | 105 | | | | | 110 | |

| | | | | | | | | | | | | | | | |
|---|---|---|---|---|---|---|---|---|---|---|---|---|---|---|---|
| Leu | Ile | Tyr | Thr | Pro | Phe | Thr | Glu | Asp | Thr | Glu | Thr | Val | Gly | Gln | Arg |
| | | | 115 | | | | | 120 | | | | | 125 | | |

| | | | | | | | | | | | | | | | |
|---|---|---|---|---|---|---|---|---|---|---|---|---|---|---|---|
| Ala | Leu | His | Ser | Ile | Leu | Asn | Ala | Ala | Ile | Met | Ile | Ser | Val | Ile | Val |
| | | | 130 | | | | | 135 | | | | | 140 | | |

| | | | | | | | | | | | | | | | |
|---|---|---|---|---|---|---|---|---|---|---|---|---|---|---|---|
| Val | Met | Thr | Ile | Leu | Leu | Val | Val | Leu | Tyr | Lys | Tyr | Arg | Cys | Tyr | Lys |
| 145 | | | | | 150 | | | | | 155 | | | | | 160 |

| | | | | | | | | | | | | | | | |
|---|---|---|---|---|---|---|---|---|---|---|---|---|---|---|---|
| Val | Ile | His | Ala | Trp | Leu | Ile | Ile | Ser | Ser | Leu | Leu | Leu | Leu | Phe | Phe |
| | | | | 165 | | | | | 170 | | | | | 175 | |

| | | | | | | | | | | | | | | | |
|---|---|---|---|---|---|---|---|---|---|---|---|---|---|---|---|
| Phe | Ser | Phe | Ile | Tyr | Leu | Gly | Glu | Val | Phe | Lys | Thr | Tyr | Asn | Val | Ala |

1

```
                180                     185                     190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
    225                 230                 235                 240

Leu Pro Glu Trp Thr Ala Trp Leu Ile Leu Ala Val Ile Ser Val Tyr
                    245                 250                 255

Asp Leu Val Ala Val Leu Cys Pro Lys Gly Pro Leu Arg Met Leu Val
                260                 265                 270

Glu Thr Ala Gln Glu Arg Asn Glu Thr Leu Phe Pro Ala Leu Ile Tyr
            275                 280                 285

Ser Ser Thr Met Val Trp Leu Val Asn Met Ala Glu Gly Asp Pro Glu
        290                 295                 300

Ala Gln Arg Arg Val Ser Lys Asn Ser Lys Tyr Asn Ala Glu Ser Thr
    305                 310                 315                 320

Glu Arg Glu Ser Gln Asp Thr Val Ala Glu Asn Asp Asp Gly Gly Phe
                    325                 330                 335

Ser Glu Glu Trp Glu Ala Gln Arg Asp Ser His Leu Gly Pro His Arg
                340                 345                 350

Ser Thr Pro Glu Ser Arg Ala Ala Val Gln Glu Leu Ser Ser Ser Ile
            355                 360                 365

Leu Ala Gly Glu Asp Pro Glu Glu Arg Gly Val Lys Leu Gly Leu Gly
        370                 375                 380

Asp Phe Ile Phe Tyr Ser Val Leu Val Gly Lys Ala Ser Ala Thr Ala
    385                 390                 395                 400

Ser Gly Asp Trp Asn Thr Thr Ile Ala Cys Phe Val Ala Ile Leu Ile
```

2

```
                405                      410                      415

Gly Leu Cys Leu Thr Leu Leu Leu Leu Ala Ile Phe Lys Lys Ala Leu
                420                  425                 430

Pro Ala Leu Pro Ile Ser Ile Thr Phe Gly Leu Val Phe Tyr Phe Ala
                435                  440                 445

Thr Asp Tyr Leu Val Gln Pro Phe Met Asp Gln Leu Ala Phe His Gln
            450                  455                 460

Phe Tyr Ile
    465
```

In the Sequence Listing SEQ ID NO: 22 should be added
<210> 22
<211> 448
<212> PRT
<213> Homo sapiens

<400> 22

```
Met Leu Thr Phe Met Ala Ser Asp Ser Glu Glu Val Cys Asp Glu
1               5                  10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Val Ala Thr Ile Lys Ser Val Arg Phe Tyr
                100                 105                 110
```

```
Pro Glu Val Phe Glu Pro Pro Leu Thr Gly Tyr Pro Gly Glu Glu Leu
            340             345             350

Glu Glu Glu Glu Glu Arg Gly Val Lys Leu Gly Leu Gly Asp Phe Ile
            355             360             365

Phe Tyr Ser Val Leu Val Gly Lys Ala Ala Ala Thr Gly Ser Gly Asp
            370             375             380

Trp Asn Thr Thr Leu Ala Cys Phe Val Ala Ile Leu Ile Gly Leu Cys
385             390             395             400

Leu Thr Leu Leu Leu Leu Ala Val Phe Lys Lys Ala Leu Pro Ala Leu
            405             410             415

Pro Ile Ser Ile Thr Phe Gly Leu Ile Phe Tyr Phe Ser Thr Asp Asn
            420             425             430

Leu Val Arg Pro Phe Met Asp Thr Leu Ala Ser His Gln Leu Tyr Ile
            435             440             445
```

```
Pro Glu Val Phe Glu Pro Pro Leu Thr Gly Tyr Pro Gly Glu Glu Leu
        340             345             350

Glu Glu Glu Glu Glu Arg Gly Val Lys Leu Gly Leu Gly Asp Phe Ile
        355             360             365

Phe Tyr Ser Val Leu Val Gly Lys Ala Ala Ala Thr Gly Ser Gly Asp
        370             375             380

Trp Asn Thr Thr Leu Ala Cys Phe Val Ala Ile Leu Ile Gly Leu Cys
385             390             395             400

Leu Thr Leu Leu Leu Leu Ala Val Phe Lys Lys Ala Leu Pro Ala Leu
                405             410             415

Pro Ile Ser Ile Thr Phe Gly Leu Ile Phe Tyr Phe Ser Thr Asp Asn
            420             425             430

Leu Val Arg Pro Phe Met Asp Thr Leu Ala Ser His Gln Leu Tyr Ile
        435             440             445
```